US009456864B2

(12) United States Patent
Witt et al.

(10) Patent No.: US 9,456,864 B2
(45) Date of Patent: Oct. 4, 2016

(54) SURGICAL INSTRUMENTS AND END EFFECTORS THEREFOR

(71) Applicant: Ethicon Endo-Surgery, Inc., Cincinnati, OH (US)

(72) Inventors: David A. Witt, Maineville, OH (US); Zhifan F. Huang, Mason, OH (US); Timothy G. Dietz, Wayne, PA (US); Raymond M. Banks, Cupertino, CA (US); Jeffrey L. Aldridge, Lebanon, OH (US); Steve G. Bernath, San Martin, CA (US); David K. Norvell, Monroe, OH (US); Patrick A. Weizman, Liberty Township, OH (US); Jason L. Harris, Lebanon, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 179 days.

(21) Appl. No.: 14/171,035

(22) Filed: Feb. 3, 2014

(65) Prior Publication Data

US 2014/0148806 A1    May 29, 2014

Related U.S. Application Data

(63) Continuation of application No. 12/781,243, filed on May 17, 2010, now Pat. No. 8,685,020.

(51) Int. Cl.
*A61B 17/29* (2006.01)
*A61B 18/14* (2006.01)
(Continued)

(52) U.S. Cl.
CPC ....... *A61B 18/1445* (2013.01); *A61B 17/3209* (2013.01); *A61B 18/148* (2013.01);
(Continued)

(58) Field of Classification Search
CPC ............ A61B 18/1445; A61B 18/148; A61B 18/1485; A61B 2018/1445; A61B 2018/0063; A61B 2018/1412; A61B 2018/00607; A61B 2017/2936; A61B 2017/2927; A61B 2017/2926; A61B 2017/2933; A61B 2017/2944; A61B 2017/2947; A61B 17/29; A61B 17/320092; A61B 17/295
See application file for complete search history.

(56) References Cited

U.S. PATENT DOCUMENTS 2,366,274 A   1/1945  Luth et al.
2,458,152 A   1/1949  Eakins
(Continued)

FOREIGN PATENT DOCUMENTS

DE    4300307 A1    7/1994
EP    0340803 B1    8/1993
(Continued)

OTHER PUBLICATIONS

Partial International Search Report for PCT/US2011/036617, Sep. 6, 2011 (2 pages).
(Continued)

*Primary Examiner* — Michael Peffley

(57) ABSTRACT

An end effector for use with a surgical instrument is disclosed. The end effector comprises a first jaw, a second jaw, wherein the first jaw is movable relative to the second jaw to transition the end effector between an open configuration and an approximated configuration to clamp tissue between the first jaw and the second jaw, and a camming assembly. The camming assembly comprises a first camming member comprising a first distal camming portion, a first proximal camming portion, and a first flexible portion extending between the first distal camming portion and the first proximal camming portion. The camming assembly further comprises a second camming member and a connector at least partially disposed between the first camming member and the second camming member, wherein the camming assembly is movable relative to the end effector to transition the end effector to the approximated configuration.

21 Claims, 22 Drawing Sheets

(51) Int. Cl.
    *A61B 17/3209*     (2006.01)
    *A61B 17/295*     (2006.01)
    *A61B 17/32*     (2006.01)
    *A61B 17/00*     (2006.01)

(52) U.S. Cl.
    CPC .......... *A61B18/1485* (2013.01); *A61B 17/295* (2013.01); *A61B 17/32* (2013.01); *A61B 2017/003* (2013.01); *A61B 2017/00738* (2013.01); *A61B 2017/00867* (2013.01); *A61B 2017/2926* (2013.01); *A61B 2017/2933* (2013.01); *A61B 2017/2934* (2013.01); *A61B 2017/2945* (2013.01); *A61B 2017/320044* (2013.01); *A61B 2018/1412* (2013.01); *A61B 2018/1432* (2013.01); *A61B 2018/1455* (2013.01); *A61B 2018/1465* (2013.01)

(56) References Cited

U.S. PATENT DOCUMENTS

| | | |
|---|---|---|
| 2,510,693 A | 6/1950 | Green |
| 2,867,039 A | 1/1959 | Zach |
| 3,166,971 A | 1/1965 | Stoecker |
| 3,525,912 A | 8/1970 | Wallin |
| 3,580,841 A | 5/1971 | Cadotte et al. |
| 3,703,651 A | 11/1972 | Blowers |
| 3,777,760 A | 12/1973 | Essner |
| 4,005,714 A | 2/1977 | Hiltebrandt |
| 4,034,762 A | 7/1977 | Cosens et al. |
| 4,058,126 A | 11/1977 | Leveen |
| 4,203,430 A | 5/1980 | Takahashi |
| 4,220,154 A | 9/1980 | Semm |
| 4,237,441 A | 12/1980 | van Konynenburg et al. |
| 4,281,785 A | 8/1981 | Brooks |
| 4,304,987 A | 12/1981 | van Konynenburg |
| 4,463,759 A | 8/1984 | Garito et al. |
| 4,492,231 A | 1/1985 | Auth |
| 4,535,773 A | 8/1985 | Yoon |
| 4,545,926 A | 10/1985 | Fouts, Jr. et al. |
| 4,550,870 A | 11/1985 | Krumme et al. |
| 4,582,236 A | 4/1986 | Hirose |
| 4,617,927 A | 10/1986 | Manes |
| 4,735,603 A | 4/1988 | Goodson et al. |
| 4,761,871 A | 8/1988 | O'Connor et al. |
| 4,830,462 A | 5/1989 | Karny et al. |
| 4,849,133 A | 7/1989 | Yoshida et al. |
| 4,860,745 A | 8/1989 | Farin et al. |
| 4,878,493 A | 11/1989 | Pasternak et al. |
| 4,880,015 A | 11/1989 | Nierman |
| 4,910,389 A | 3/1990 | Sherman et al. |
| 4,920,978 A | 5/1990 | Colvin |
| 4,936,842 A | 6/1990 | D'Amelio et al. |
| 5,020,514 A | 6/1991 | Heckele |
| 5,061,269 A | 10/1991 | Muller |
| 5,099,840 A | 3/1992 | Goble et al. |
| 5,104,025 A | 4/1992 | Main et al. |
| 5,106,538 A | 4/1992 | Barma et al. |
| 5,108,383 A | 4/1992 | White |
| 5,156,633 A | 10/1992 | Smith |
| 5,160,334 A | 11/1992 | Billings et al. |
| 5,190,541 A | 3/1993 | Abele et al. |
| 5,196,007 A | 3/1993 | Ellman et al. |
| 5,205,459 A | 4/1993 | Brinkerhoff et al. |
| 5,217,460 A | 6/1993 | Knoepfler |
| 5,234,428 A | 8/1993 | Kaufman |
| 5,258,006 A | 11/1993 | Rydell et al. |
| 5,285,945 A | 2/1994 | Brinkerhoff et al. |
| 5,290,286 A | 3/1994 | Parins |
| 5,309,927 A | 5/1994 | Welch |
| 5,318,564 A | 6/1994 | Eggers |
| 5,318,589 A | 6/1994 | Lichtman |
| 5,330,471 A | 7/1994 | Eggers |
| 5,330,502 A | 7/1994 | Hassler et al. |
| 5,339,723 A | 8/1994 | Huitema |
| 5,342,359 A | 8/1994 | Rydell |
| 5,361,583 A | 11/1994 | Huitema |
| 5,383,874 A | 1/1995 | Jackson et al. |
| 5,387,207 A | 2/1995 | Dyer et al. |
| 5,389,098 A | 2/1995 | Tsuruta et al. |
| 5,395,312 A | 3/1995 | Desai |
| 5,395,363 A | 3/1995 | Billings et al. |
| 5,395,364 A | 3/1995 | Anderhub et al. |
| 5,396,900 A | 3/1995 | Slater et al. |
| 5,403,312 A | 4/1995 | Yates et al. |
| 5,417,709 A | 5/1995 | Slater |
| 5,428,504 A | 6/1995 | Bhatla |
| 5,429,131 A | 7/1995 | Scheinman et al. |
| 5,443,463 A | 8/1995 | Stern et al. |
| 5,445,638 A | 8/1995 | Rydell et al. |
| 5,451,227 A | 9/1995 | Michaelson |
| 5,458,598 A | 10/1995 | Feinberg et al. |
| 5,465,895 A | 11/1995 | Knodel et al. |
| 5,472,443 A | 12/1995 | Cordis et al. |
| 5,476,479 A | 12/1995 | Green et al. |
| 5,480,409 A | 1/1996 | Riza |
| 5,484,436 A | 1/1996 | Eggers et al. |
| 5,486,189 A | 1/1996 | Mudry et al. |
| 5,496,317 A | 3/1996 | Goble et al. |
| 5,504,650 A | 4/1996 | Katsui et al. |
| 5,509,922 A | 4/1996 | Aranyi et al. |
| 5,511,556 A | 4/1996 | DeSantis |
| 5,520,704 A | 5/1996 | Castro et al. |
| 5,522,839 A | 6/1996 | Pilling |
| 5,531,744 A | 7/1996 | Nardella et al. |
| 5,542,916 A | 8/1996 | Hirsch et al. |
| 5,558,671 A | 9/1996 | Yates |
| 5,563,179 A | 10/1996 | Stone et al. |
| 5,571,121 A | 11/1996 | Heifetz |
| 5,573,534 A | 11/1996 | Stone |
| 5,584,830 A | 12/1996 | Ladd et al. |
| 5,599,350 A | 2/1997 | Schulze et al. |
| 5,607,450 A | 3/1997 | Zvenyatsky et al. |
| 5,611,813 A | 3/1997 | Lichtman |
| 5,618,307 A | 4/1997 | Donlon et al. |
| 5,624,452 A | 4/1997 | Yates |
| 5,632,432 A | 5/1997 | Schulze et al. |
| 5,647,871 A | 7/1997 | Levine et al. |
| 5,658,281 A | 8/1997 | Heard |
| 5,662,667 A | 9/1997 | Knodel |
| 5,665,085 A | 9/1997 | Nardella |
| 5,665,100 A | 9/1997 | Yoon |
| 5,674,219 A | 10/1997 | Monson et al. |
| 5,674,220 A | 10/1997 | Fox et al. |
| 5,688,270 A | 11/1997 | Yates et al. |
| 5,693,051 A | 12/1997 | Schulze et al. |
| 5,709,680 A | 1/1998 | Yates et al. |
| 5,713,896 A | 2/1998 | Nardella |
| 5,716,366 A | 2/1998 | Yates |
| 5,735,848 A | 4/1998 | Yates et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,796,188 A | 8/1998 | Bays |
| 5,797,941 A | 8/1998 | Schulze et al. |
| 5,800,432 A | 9/1998 | Swanson |
| 5,800,449 A | 9/1998 | Wales |
| 5,807,393 A | 9/1998 | Williamson, IV et al. |
| 5,810,811 A | 9/1998 | Yates et al. |
| 5,817,033 A | 10/1998 | DeSantis et al. |
| 5,817,084 A | 10/1998 | Jensen |
| 5,817,093 A | 10/1998 | Williamson, IV et al. |
| 5,836,909 A | 11/1998 | Cosmescu |
| 5,836,943 A | 11/1998 | Miller, III |
| 5,853,412 A | 12/1998 | Mayenberger |
| 5,876,401 A | 3/1999 | Schulze et al. |
| 5,878,193 A | 3/1999 | Wang et al. |
| 5,880,668 A | 3/1999 | Hall |
| 5,891,142 A | 4/1999 | Eggers et al. |

(56) References Cited

U.S. PATENT DOCUMENTS

| | | |
|---|---|---|
| 5,906,625 A | 5/1999 | Bito et al. |
| 5,921,956 A | 7/1999 | Grinberg et al. |
| 5,984,938 A | 11/1999 | Yoon |
| 6,003,517 A | 12/1999 | Sheffield et al. |
| 6,013,052 A | 1/2000 | Durman et al. |
| 6,024,741 A | 2/2000 | Williamson, IV et al. |
| 6,024,744 A | 2/2000 | Kese et al. |
| 6,033,399 A | 3/2000 | Gines |
| 6,039,734 A | 3/2000 | Goble |
| 6,050,996 A | 4/2000 | Schmaltz et al. |
| 6,063,098 A | 5/2000 | Houser et al. |
| 6,068,629 A | 5/2000 | Haissaguerre et al. |
| 6,074,389 A | 6/2000 | Levine et al. |
| 6,091,995 A | 7/2000 | Ingle et al. |
| 6,099,483 A | 8/2000 | Palmer et al. |
| 6,099,550 A | 8/2000 | Yoon |
| H1904 H | 10/2000 | Yates et al. |
| 6,132,368 A | 10/2000 | Cooper |
| 6,144,402 A | 11/2000 | Norsworthy et al. |
| 6,152,923 A | 11/2000 | Ryan |
| 6,162,208 A | 12/2000 | Hipps |
| 6,174,309 B1 | 1/2001 | Wrublewski et al. |
| 6,190,386 B1 | 2/2001 | Rydell |
| 6,206,876 B1 | 3/2001 | Levine et al. |
| 6,228,080 B1 | 5/2001 | Gines |
| 6,231,565 B1 | 5/2001 | Tovey et al. |
| 6,259,230 B1 | 7/2001 | Chou |
| 6,277,117 B1 | 8/2001 | Tetzlaff et al. |
| 6,292,700 B1 | 9/2001 | Morrison et al. |
| 6,325,799 B1 | 12/2001 | Goble |
| 6,340,878 B1 | 1/2002 | Oglesbee |
| 6,364,888 B1 | 4/2002 | Niemeyer et al. |
| 6,391,026 B1 | 5/2002 | Hung et al. |
| 6,398,779 B1 | 6/2002 | Buysse et al. |
| H2037 H | 7/2002 | Yates et al. |
| 6,419,675 B1 | 7/2002 | Gallo, Sr. |
| 6,430,446 B1 | 8/2002 | Knowlton |
| 6,443,968 B1 | 9/2002 | Holthaus et al. |
| 6,458,128 B1 | 10/2002 | Schulze |
| 6,464,702 B2 | 10/2002 | Schulze et al. |
| 6,491,690 B1 | 12/2002 | Goble et al. |
| 6,500,112 B1 | 12/2002 | Khouri |
| 6,500,176 B1 * | 12/2002 | Truckai ............... A61B 18/1445 606/205 |
| 6,503,248 B1 | 1/2003 | Levine |
| 6,511,480 B1 | 1/2003 | Tetzlaff et al. |
| 6,514,252 B2 | 2/2003 | Nezhat et al. |
| 6,517,565 B1 | 2/2003 | Whitman et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,554,829 B2 | 4/2003 | Schulze et al. |
| 6,558,376 B2 | 5/2003 | Bishop |
| 6,572,639 B1 | 6/2003 | Ingle et al. |
| 6,575,969 B1 | 6/2003 | Rittman, III et al. |
| 6,584,360 B2 | 6/2003 | Francischelli et al. |
| 6,585,735 B1 | 7/2003 | Frazier et al. |
| 6,589,200 B1 | 7/2003 | Schwemberger et al. |
| 6,602,252 B2 | 8/2003 | Mollenauer |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,635,057 B2 | 10/2003 | Harano et al. |
| 6,651,669 B1 | 11/2003 | Burnside |
| 6,656,177 B2 * | 12/2003 | Truckai ............... A61B 18/1445 606/205 |
| 6,656,198 B2 | 12/2003 | Tsonton et al. |
| 6,673,248 B2 | 1/2004 | Chowdhury |
| 6,679,882 B1 | 1/2004 | Kornerup |
| 6,695,840 B2 | 2/2004 | Schulze |
| 6,722,552 B2 | 4/2004 | Fenton, Jr. |
| 6,770,072 B1 | 8/2004 | Truckai et al. |
| 6,773,409 B2 | 8/2004 | Truckai et al. |
| 6,773,435 B2 | 8/2004 | Schulze et al. |
| 6,775,575 B2 | 8/2004 | Bommannan et al. |
| 6,783,524 B2 | 8/2004 | Anderson et al. |
| 6,789,939 B2 | 9/2004 | Schrödinger et al. |
| 6,796,981 B2 | 9/2004 | Wham et al. |
| 6,800,085 B2 | 10/2004 | Selmon et al. |
| 6,802,843 B2 | 10/2004 | Truckai et al. |
| 6,811,842 B1 | 11/2004 | Ehrnsperger et al. |
| 6,821,273 B2 | 11/2004 | Mollenauer |
| 6,835,199 B2 | 12/2004 | McGuckin, Jr. et al. |
| 6,840,938 B1 | 1/2005 | Morley et al. |
| 6,860,880 B2 | 3/2005 | Treat et al. |
| 6,905,497 B2 * | 6/2005 | Truckai ............... A61B 18/1442 606/49 |
| 6,908,463 B2 | 6/2005 | Treat et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,644 B2 | 8/2005 | Truckai et al. |
| 6,953,461 B2 | 10/2005 | McClurken et al. |
| 6,994,709 B2 | 2/2006 | Iida |
| 7,000,818 B2 | 2/2006 | Shelton, IV et al. |
| 7,011,657 B2 | 3/2006 | Truckai et al. |
| 7,041,102 B2 | 5/2006 | Truckai et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,936 B2 | 6/2006 | Ryan |
| 7,070,597 B2 | 7/2006 | Truckai et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,094,235 B2 | 8/2006 | Francischelli et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,112,201 B2 | 9/2006 | Truckai et al. |
| 7,118,570 B2 | 10/2006 | Tetzlaff et al. |
| 7,125,409 B2 | 10/2006 | Truckai et al. |
| 7,131,970 B2 | 11/2006 | Moses et al. |
| 7,137,980 B2 | 11/2006 | Buysse et al. |
| 7,143,925 B2 | 12/2006 | Shelton, IV et al. |
| 7,147,138 B2 | 12/2006 | Shelton, IV |
| 7,156,846 B2 | 1/2007 | Dycus et al. |
| 7,160,296 B2 | 1/2007 | Pearson et al. |
| 7,169,146 B2 | 1/2007 | Truckai et al. |
| 7,169,156 B2 | 1/2007 | Hart |
| 7,186,253 B2 | 3/2007 | Truckai et al. |
| 7,189,233 B2 | 3/2007 | Truckai et al. |
| 7,195,631 B2 | 3/2007 | Dumbauld |
| 7,207,471 B2 | 4/2007 | Heinrich et al. |
| 7,220,951 B2 | 5/2007 | Truckai et al. |
| 7,225,964 B2 | 6/2007 | Mastri et al. |
| 7,226,448 B2 | 6/2007 | Bertolero et al. |
| 7,232,440 B2 | 6/2007 | Dumbauld et al. |
| 7,235,073 B2 | 6/2007 | Levine et al. |
| 7,241,294 B2 | 7/2007 | Reschke |
| 7,251,531 B2 | 7/2007 | Mosher et al. |
| 7,252,667 B2 | 8/2007 | Moses et al. |
| 7,267,677 B2 | 9/2007 | Johnson et al. |
| 7,267,685 B2 | 9/2007 | Butaric et al. |
| 7,287,682 B1 | 10/2007 | Ezzat et al. |
| 7,303,557 B2 | 12/2007 | Wham et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,329,257 B2 | 2/2008 | Kanehira et al. |
| 7,354,440 B2 | 4/2008 | Truckai et al. |
| 7,357,287 B2 | 4/2008 | Shelton, IV et al. |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,381,209 B2 | 6/2008 | Truckai et al. |
| 7,384,420 B2 | 6/2008 | Dycus et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,422,139 B2 | 9/2008 | Shelton, IV et al. |
| 7,435,582 B2 | 10/2008 | Zimmermann et al. |

(56) References Cited

U.S. PATENT DOCUMENTS

| | | |
|---|---|---|
| 7,442,193 B2 | 10/2008 | Shields et al. |
| 7,445,621 B2 | 11/2008 | Dumbauld et al. |
| 7,464,846 B2 | 12/2008 | Shelton, IV et al. |
| 7,473,253 B2 | 1/2009 | Dycus et al. |
| 7,488,319 B2 | 2/2009 | Yates |
| 7,491,201 B2 | 2/2009 | Shields et al. |
| 7,494,501 B2 | 2/2009 | Ahlberg et al. |
| 7,498,080 B2 | 3/2009 | Tung et al. |
| 7,510,107 B2 | 3/2009 | Timm et al. |
| 7,513,025 B2 | 4/2009 | Fischer |
| 7,517,349 B2 | 4/2009 | Truckai et al. |
| 7,524,320 B2 | 4/2009 | Tierney et al. |
| 7,540,872 B2 | 6/2009 | Schechter et al. |
| 7,550,216 B2 | 6/2009 | Ofer et al. |
| 7,559,452 B2 | 7/2009 | Wales et al. |
| 7,582,086 B2 | 9/2009 | Privitera et al. |
| 7,586,289 B2 | 9/2009 | Andruk et al. |
| 7,588,176 B2 | 9/2009 | Timm et al. |
| 7,594,925 B2 | 9/2009 | Danek et al. |
| 7,597,693 B2 | 10/2009 | Garrison |
| 7,604,150 B2 | 10/2009 | Boudreaux |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,277 B2 | 1/2010 | McClurken et al. |
| 7,648,499 B2 | 1/2010 | Orszulak et al. |
| 7,658,311 B2 | 2/2010 | Boudreaux |
| 7,665,647 B2 | 2/2010 | Shelton, IV et al. |
| 7,666,206 B2 | 2/2010 | Taniguchi et al. |
| 7,691,095 B2 | 4/2010 | Bednarek et al. |
| 7,691,098 B2 | 4/2010 | Wallace et al. |
| 7,703,459 B2 | 4/2010 | Saadat et al. |
| 7,703,653 B2 | 4/2010 | Shah et al. |
| 7,708,751 B2 | 5/2010 | Hughes et al. |
| 7,722,527 B2 | 5/2010 | Bouchier et al. |
| 7,722,607 B2 | 5/2010 | Dumbauld et al. |
| 7,753,904 B2 | 7/2010 | Shelton, IV et al. |
| 7,753,908 B2 | 7/2010 | Swanson |
| 7,762,445 B2 | 7/2010 | Heinrich et al. |
| 7,766,910 B2 | 8/2010 | Hixson et al. |
| 7,776,037 B2 | 8/2010 | Odom |
| 7,780,663 B2 | 8/2010 | Yates et al. |
| 7,784,663 B2 | 8/2010 | Shelton, IV |
| 7,789,883 B2 | 9/2010 | Takashino et al. |
| 7,803,156 B2 | 9/2010 | Eder et al. |
| 7,806,891 B2 | 10/2010 | Nowlin et al. |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,872 B2 | 10/2010 | Johnson et al. |
| 7,824,401 B2 | 11/2010 | Manzo et al. |
| 7,832,408 B2 | 11/2010 | Shelton, IV et al. |
| 7,832,612 B2 | 11/2010 | Baxter, III et al. |
| 7,846,159 B2 | 12/2010 | Morrison et al. |
| 7,846,160 B2 | 12/2010 | Payne et al. |
| 7,879,035 B2 | 2/2011 | Garrison et al. |
| 7,879,070 B2 | 2/2011 | Ortiz et al. |
| 7,896,875 B2 | 3/2011 | Heim et al. |
| 7,901,400 B2 | 3/2011 | Wham et al. |
| 7,909,220 B2 | 3/2011 | Viola |
| 7,919,184 B2 | 4/2011 | Mohapatra et al. |
| 7,931,649 B2 | 4/2011 | Couture et al. |
| 7,935,114 B2 | 5/2011 | Takashino et al. |
| 7,955,331 B2 | 6/2011 | Truckai et al. |
| 7,963,963 B2 | 6/2011 | Francischelli et al. |
| 7,967,602 B2 | 6/2011 | Lindquist |
| 7,981,113 B2 | 7/2011 | Truckai et al. |
| 7,997,278 B2 | 8/2011 | Utley et al. |
| 8,020,743 B2 | 9/2011 | Shelton, IV |
| 8,056,720 B2 | 11/2011 | Hawkes |
| 8,058,771 B2 | 11/2011 | Giordano et al. |
| 8,070,036 B1 | 12/2011 | Knodel et al. |
| 8,105,323 B2 | 1/2012 | Buysse et al. |
| 8,128,624 B2 | 3/2012 | Couture et al. |
| 8,136,712 B2 | 3/2012 | Zingman |
| 8,141,762 B2 | 3/2012 | Bedi et al. |
| 8,157,145 B2 | 4/2012 | Shelton, IV et al. |
| 8,197,472 B2 | 6/2012 | Lau et al. |
| 8,197,479 B2 | 6/2012 | Olson et al. |
| 8,221,415 B2 | 7/2012 | Francischelli |
| 8,241,235 B2 | 8/2012 | Kahler et al. |
| 8,246,615 B2 | 8/2012 | Behnke |
| 8,246,618 B2 | 8/2012 | Bucciaglia et al. |
| 8,251,994 B2 | 8/2012 | McKenna et al. |
| 8,262,563 B2 | 9/2012 | Bakos et al. |
| 8,267,300 B2 | 9/2012 | Boudreaux |
| 8,277,446 B2 | 10/2012 | Heard |
| 8,277,447 B2 | 10/2012 | Garrison et al. |
| 8,282,669 B2 | 10/2012 | Gerber et al. |
| 8,287,528 B2 | 10/2012 | Wham et al. |
| 8,292,886 B2 | 10/2012 | Kerr et al. |
| 8,298,232 B2 | 10/2012 | Unger |
| 8,303,583 B2 | 11/2012 | Hosier et al. |
| 8,323,310 B2 | 12/2012 | Kingsley |
| 8,357,158 B2 | 1/2013 | McKenna et al. |
| 8,377,059 B2 | 2/2013 | Deville et al. |
| 8,397,971 B2 | 3/2013 | Yates et al. |
| 8,414,577 B2 | 4/2013 | Boudreaux et al. |
| 8,430,876 B2 | 4/2013 | Kappus et al. |
| 8,453,906 B2 | 6/2013 | Huang et al. |
| 8,460,288 B2 | 6/2013 | Tamai et al. |
| 8,460,292 B2 | 6/2013 | Truckai et al. |
| 8,486,057 B2 | 7/2013 | Behnke, II |
| 8,496,682 B2 | 7/2013 | Guerra et al. |
| 8,535,311 B2 | 9/2013 | Schall |
| 8,540,128 B2 | 9/2013 | Shelton, IV et al. |
| 8,562,598 B2 | 10/2013 | Falkenstein et al. |
| 8,562,604 B2 | 10/2013 | Nishimura |
| 8,568,390 B2 | 10/2013 | Mueller |
| 8,568,412 B2 | 10/2013 | Brandt et al. |
| 8,569,997 B2 | 10/2013 | Lee |
| 8,574,231 B2 | 11/2013 | Boudreaux et al. |
| 8,591,506 B2 | 11/2013 | Wham et al. |
| 8,613,383 B2 | 12/2013 | Beckman et al. |
| 8,623,044 B2 | 1/2014 | Timm et al. |
| 8,628,529 B2 | 1/2014 | Aldridge et al. |
| 8,632,461 B2 | 1/2014 | Glossop |
| 8,647,350 B2 | 2/2014 | Mohan et al. |
| 8,663,222 B2 | 3/2014 | Anderson et al. |
| 8,684,253 B2 | 4/2014 | Giordano et al. |
| 8,685,020 B2 | 4/2014 | Weizman et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,709,035 B2 | 4/2014 | Johnson et al. |
| 8,715,270 B2 | 5/2014 | Weitzner et al. |
| 8,715,277 B2 | 5/2014 | Weizman |
| 8,734,443 B2 | 5/2014 | Hixson et al. |
| 8,747,238 B2 | 6/2014 | Shelton, IV et al. |
| 8,747,404 B2 | 6/2014 | Boudreaux et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,764,747 B2 | 7/2014 | Cummings et al. |
| 8,790,342 B2 | 7/2014 | Stulen et al. |
| 8,795,276 B2 | 8/2014 | Dietz et al. |
| 8,834,466 B2 | 9/2014 | Cummings et al. |
| 8,834,518 B2 | 9/2014 | Faller et al. |
| 8,845,630 B2 | 9/2014 | Mehta et al. |
| 8,888,776 B2 | 11/2014 | Dietz et al. |
| 8,906,016 B2 | 12/2014 | Boudreaux et al. |
| 8,926,607 B2 | 1/2015 | Norvell et al. |
| 8,926,608 B2 | 1/2015 | Bacher et al. |
| 8,931,682 B2 | 1/2015 | Timm et al. |
| 8,939,974 B2 | 1/2015 | Boudreaux et al. |
| 8,951,248 B2 | 2/2015 | Messerly et al. |
| 8,956,349 B2 | 2/2015 | Aldridge et al. |
| 8,979,843 B2 | 3/2015 | Timm et al. |
| 8,979,844 B2 | 3/2015 | White et al. |
| 8,979,890 B2 | 3/2015 | Boudreaux |

(56) References Cited

U.S. PATENT DOCUMENTS

| | | |
|---|---|---|
| 8,986,302 B2 | 3/2015 | Aldridge et al. |
| 8,992,422 B2 | 3/2015 | Spivey et al. |
| 9,005,199 B2 | 4/2015 | Beckman et al. |
| 9,011,437 B2 | 4/2015 | Woodruff et al. |
| 9,028,494 B2 | 5/2015 | Shelton, IV et al. |
| 9,028,519 B2 | 5/2015 | Yates et al. |
| 9,044,243 B2 | 6/2015 | Johnson et al. |
| 9,044,256 B2 | 6/2015 | Cadeddu et al. |
| 9,060,770 B2 | 6/2015 | Shelton, IV et al. |
| 9,072,535 B2 | 7/2015 | Shelton, IV et al. |
| 9,072,536 B2 | 7/2015 | Shelton, IV et al. |
| 9,101,385 B2 | 8/2015 | Shelton, IV et al. |
| 9,119,657 B2 | 9/2015 | Shelton, IV et al. |
| 9,125,662 B2 | 9/2015 | Shelton, IV |
| 9,149,324 B2 | 10/2015 | Huang et al. |
| 9,179,912 B2 | 11/2015 | Yates et al. |
| 9,192,431 B2 | 11/2015 | Woodruff et al. |
| 9,204,879 B2 | 12/2015 | Shelton, IV |
| 9,226,751 B2 | 1/2016 | Shelton, IV et al. |
| 9,237,891 B2 | 1/2016 | Shelton, IV |
| 9,259,265 B2 | 2/2016 | Harris et al. |
| 9,265,926 B2 | 2/2016 | Strobl et al. |
| 9,283,027 B2 | 3/2016 | Monson et al. |
| 9,295,514 B2 | 3/2016 | Shelton, IV et al. |
| 9,314,292 B2 | 4/2016 | Trees et al. |
| 2002/0022836 A1 | 2/2002 | Goble et al. |
| 2002/0165541 A1 | 11/2002 | Whitman |
| 2003/0014053 A1 | 1/2003 | Nguyen et al. |
| 2003/0105474 A1 | 6/2003 | Bonutti |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0158548 A1 | 8/2003 | Phan et al. |
| 2003/0216722 A1 | 11/2003 | Swanson |
| 2003/0229344 A1 | 12/2003 | Dycus et al. |
| 2004/0019350 A1 | 1/2004 | O'Brien et al. |
| 2004/0092992 A1 | 5/2004 | Adams et al. |
| 2004/0138621 A1 | 7/2004 | Jahns et al. |
| 2004/0167508 A1 | 8/2004 | Wham et al. |
| 2004/0193150 A1 | 9/2004 | Sharkey et al. |
| 2004/0232196 A1 | 11/2004 | Shelton, IV et al. |
| 2004/0249374 A1 | 12/2004 | Tetzlaff et al. |
| 2004/0260273 A1 | 12/2004 | Wan |
| 2005/0015125 A1 | 1/2005 | Mioduski et al. |
| 2005/0033278 A1 | 2/2005 | McClurken et al. |
| 2005/0085809 A1 | 4/2005 | Mucko et al. |
| 2005/0090817 A1 | 4/2005 | Phan |
| 2005/0131390 A1 | 6/2005 | Heinrich et al. |
| 2005/0165429 A1 | 7/2005 | Douglas et al. |
| 2005/0171522 A1 | 8/2005 | Christopherson |
| 2005/0203507 A1 | 9/2005 | Truckai et al. |
| 2005/0261581 A1 | 11/2005 | Hughes et al. |
| 2005/0267464 A1 | 12/2005 | Truckai et al. |
| 2006/0052778 A1 | 3/2006 | Chapman et al. |
| 2006/0064086 A1 | 3/2006 | Odom |
| 2006/0069388 A1 | 3/2006 | Truckai et al. |
| 2006/0159731 A1 | 7/2006 | Shoshan |
| 2006/0270916 A1 | 11/2006 | Skwarek et al. |
| 2006/0293656 A1 | 12/2006 | Shadduck et al. |
| 2007/0027469 A1 | 2/2007 | Smith et al. |
| 2007/0073185 A1 | 3/2007 | Nakao |
| 2007/0073341 A1 | 3/2007 | Smith et al. |
| 2007/0106158 A1 | 5/2007 | Madan et al. |
| 2007/0146113 A1 | 6/2007 | Truckai et al. |
| 2007/0173803 A1 | 7/2007 | Wham et al. |
| 2007/0173813 A1 | 7/2007 | Odom |
| 2007/0185474 A1 | 8/2007 | Nahen |
| 2007/0191713 A1 | 8/2007 | Eichmann et al. |
| 2007/0191830 A1 | 8/2007 | Cromton, Jr. et al. |
| 2007/0203483 A1 | 8/2007 | Kim et al. |
| 2007/0208312 A1 | 9/2007 | Norton et al. |
| 2007/0232920 A1 | 10/2007 | Kowalski et al. |
| 2007/0232926 A1 | 10/2007 | Stulen et al. |
| 2007/0232927 A1 | 10/2007 | Madan et al. |
| 2007/0232928 A1 | 10/2007 | Wiener et al. |
| 2007/0236213 A1 | 10/2007 | Paden et al. |
| 2007/0239025 A1 | 10/2007 | Wiener et al. |
| 2007/0260242 A1 | 11/2007 | Dycus et al. |
| 2007/0265613 A1 | 11/2007 | Edelstein et al. |
| 2008/0015575 A1 | 1/2008 | Odom et al. |
| 2008/0071269 A1 | 3/2008 | Hilario et al. |
| 2008/0114355 A1 | 5/2008 | Whayne et al. |
| 2008/0147058 A1 | 6/2008 | Horrell et al. |
| 2008/0147062 A1 | 6/2008 | Truckai et al. |
| 2008/0167522 A1 | 7/2008 | Giordano et al. |
| 2008/0188755 A1 | 8/2008 | Hart |
| 2008/0188851 A1 | 8/2008 | Truckai et al. |
| 2008/0188912 A1 | 8/2008 | Stone et al. |
| 2008/0221565 A1 | 9/2008 | Eder et al. |
| 2008/0262491 A1 | 10/2008 | Swoyer et al. |
| 2008/0269862 A1 | 10/2008 | Elmouelhi et al. |
| 2008/0281315 A1 | 11/2008 | Gines |
| 2008/0294158 A1 | 11/2008 | Pappone et al. |
| 2009/0012516 A1 | 1/2009 | Curtis et al. |
| 2009/0048589 A1 | 2/2009 | Takashino et al. |
| 2009/0076506 A1 | 3/2009 | Baker |
| 2009/0076534 A1 | 3/2009 | Shelton, IV et al. |
| 2009/0099582 A1 | 4/2009 | Isaacs et al. |
| 2009/0125026 A1 | 5/2009 | Rioux et al. |
| 2009/0125027 A1 | 5/2009 | Fischer |
| 2009/0138003 A1 | 5/2009 | Deville et al. |
| 2009/0138006 A1 | 5/2009 | Bales et al. |
| 2009/0182332 A1 | 7/2009 | Long et al. |
| 2009/0206140 A1 | 8/2009 | Scheib et al. |
| 2009/0209979 A1 | 8/2009 | Yates et al. |
| 2009/0248002 A1 | 10/2009 | Takashino et al. |
| 2009/0248021 A1 | 10/2009 | McKenna |
| 2009/0320268 A1 | 12/2009 | Cunningham et al. |
| 2009/0326530 A1 | 12/2009 | Orban, III et al. |
| 2010/0032470 A1 | 2/2010 | Hess et al. |
| 2010/0036370 A1 | 2/2010 | Mirel et al. |
| 2010/0036380 A1 | 2/2010 | Taylor et al. |
| 2010/0076433 A1 | 3/2010 | Taylor et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0094323 A1 | 4/2010 | Isaacs et al. |
| 2010/0168620 A1 | 7/2010 | Klimovitch et al. |
| 2010/0222752 A1 | 9/2010 | Collins, Jr. et al. |
| 2010/0237132 A1 | 9/2010 | Measamer et al. |
| 2010/0264194 A1 | 10/2010 | Huang et al. |
| 2010/0274278 A1 | 10/2010 | Fleenor et al. |
| 2011/0015627 A1 | 1/2011 | DiNardo et al. |
| 2011/0082486 A1 | 4/2011 | Messerly et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087220 A1 | 4/2011 | Felder et al. |
| 2011/0118754 A1 | 5/2011 | Dachs, II et al. |
| 2011/0155781 A1 | 6/2011 | Swensgard et al. |
| 2011/0224668 A1 | 9/2011 | Johnson et al. |
| 2011/0276049 A1 | 11/2011 | Gerhardt |
| 2011/0276057 A1 | 11/2011 | Conlon et al. |
| 2011/0284014 A1 | 11/2011 | Cadeddu et al. |
| 2011/0290856 A1 | 12/2011 | Shelton, IV et al. |
| 2011/0295269 A1 | 12/2011 | Swensgard et al. |
| 2011/0295295 A1 | 12/2011 | Shelton, IV et al. |
| 2011/0301605 A1 | 12/2011 | Horner |
| 2011/0306967 A1 | 12/2011 | Payne et al. |
| 2012/0016413 A1 | 1/2012 | Timm et al. |
| 2012/0022519 A1 | 1/2012 | Huang et al. |
| 2012/0022525 A1* | 1/2012 | Dietz ............... A61B 17/32 606/45 |
| 2012/0022526 A1 | 1/2012 | Aldridge et al. |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0078248 A1 | 3/2012 | Worrell et al. |
| 2012/0083783 A1 | 4/2012 | Davison et al. |

(56) References Cited

U.S. PATENT DOCUMENTS

| | | |
|---|---|---|
| 2012/0109186 A1 | 5/2012 | Parrott et al. |
| 2012/0116265 A1 | 5/2012 | Houser et al. |
| 2012/0116379 A1 | 5/2012 | Yates et al. |
| 2012/0116380 A1 | 5/2012 | Madan et al. |
| 2012/0116391 A1 | 5/2012 | Houser et al. |
| 2012/0130256 A1 | 5/2012 | Buysse et al. |
| 2012/0136353 A1 | 5/2012 | Romero |
| 2012/0150170 A1 | 6/2012 | Buysse et al. |
| 2012/0150192 A1 | 6/2012 | Dachs, II et al. |
| 2012/0172859 A1 | 7/2012 | Condie et al. |
| 2012/0265196 A1 | 10/2012 | Turner et al. |
| 2013/0023925 A1 | 1/2013 | Mueller |
| 2013/0030433 A1 | 1/2013 | Heard |
| 2013/0079762 A1 | 3/2013 | Twomey et al. |
| 2013/0085496 A1 | 4/2013 | Unger et al. |
| 2013/0103023 A1 | 4/2013 | Monson et al. |
| 2013/0103024 A1 | 4/2013 | Monson et al. |
| 2013/0123776 A1 | 5/2013 | Monson et al. |
| 2013/0131660 A1 | 5/2013 | Monson et al. |
| 2013/0253256 A1 | 9/2013 | Griffith et al. |
| 2013/0253502 A1 | 9/2013 | Aronow et al. |
| 2013/0338661 A1 | 12/2013 | Behnke, II |
| 2014/0001231 A1 | 1/2014 | Shelton, IV et al. |
| 2014/0001234 A1 | 1/2014 | Shelton, IV et al. |
| 2014/0001235 A1 | 1/2014 | Shelton, IV |
| 2014/0001236 A1 | 1/2014 | Shelton, IV et al. |
| 2014/0005640 A1 | 1/2014 | Shelton, IV et al. |
| 2014/0005653 A1 | 1/2014 | Shelton, IV et al. |
| 2014/0005678 A1 | 1/2014 | Shelton, IV et al. |
| 2014/0005680 A1 | 1/2014 | Shelton, IV et al. |
| 2014/0005693 A1 | 1/2014 | Shelton, IV et al. |
| 2014/0005694 A1 | 1/2014 | Shelton, IV et al. |
| 2014/0005695 A1 | 1/2014 | Shelton, IV |
| 2014/0005718 A1 | 1/2014 | Shelton, IV et al. |
| 2014/0014544 A1 | 1/2014 | Bugnard et al. |
| 2014/0094801 A1 | 4/2014 | Boudreaux et al. |
| 2014/0194914 A1 | 7/2014 | Hunt et al. |
| 2014/0194915 A1 | 7/2014 | Johnson et al. |
| 2014/0257284 A1 | 9/2014 | Artale |
| 2014/0330271 A1 | 11/2014 | Dietz et al. |
| 2014/0343550 A1 | 11/2014 | Faller et al. |
| 2015/0018826 A1 | 1/2015 | Boudreaux |
| 2015/0080876 A1 | 3/2015 | Worrell et al. |
| 2015/0080879 A1 | 3/2015 | Trees et al. |
| 2015/0080891 A1 | 3/2015 | Shelton, IV et al. |
| 2015/0133915 A1 | 5/2015 | Strobl et al. |
| 2015/0190189 A1 | 7/2015 | Yates et al. |
| 2015/0196352 A1 | 7/2015 | Beckman et al. |
| 2015/0201953 A1 | 7/2015 | Strobl et al. |
| 2015/0230853 A1 | 8/2015 | Johnson et al. |
| 2015/0265347 A1 | 9/2015 | Yates et al. |
| 2015/0272602 A1 | 10/2015 | Boudreaux et al. |
| 2015/0272657 A1 | 10/2015 | Yates et al. |
| 2015/0272659 A1 | 10/2015 | Boudreaux et al. |
| 2015/0272660 A1 | 10/2015 | Boudreaux et al. |
| 2015/0289925 A1 | 10/2015 | Voegele et al. |
| 2015/0297286 A1 | 10/2015 | Boudreaux et al. |
| 2016/0051315 A1 | 2/2016 | Boudreaux |
| 2016/0051316 A1 | 2/2016 | Boudreaux |
| 2016/0051317 A1 | 2/2016 | Boudreaux |
| 2016/0058492 A1 | 3/2016 | Yates et al. |
| 2016/0074108 A1 | 3/2016 | Woodruff et al. |

FOREIGN PATENT DOCUMENTS

| | | |
|---|---|---|
| EP | 0630612 A1 | 12/1994 |
| EP | 0705571 A1 | 4/1996 |
| EP | 0557806 B1 | 5/1998 |
| EP | 0640317 B1 | 9/1999 |
| EP | 0722696 B1 | 12/2002 |
| EP | 1293172 B1 | 4/2006 |
| EP | 1749479 A1 | 2/2007 |
| EP | 1767157 A1 | 3/2007 |
| EP | 1878399 A1 | 1/2008 |
| EP | 1915953 A1 | 4/2008 |
| EP | 1532933 B1 | 5/2008 |
| EP | 1707143 B1 | 6/2008 |
| EP | 1943957 A2 | 7/2008 |
| EP | 1849424 B1 | 4/2009 |
| EP | 2042117 A1 | 4/2009 |
| EP | 2060238 A1 | 5/2009 |
| EP | 1810625 B1 | 8/2009 |
| EP | 2090238 A1 | 8/2009 |
| EP | 2090256 A2 | 8/2009 |
| EP | 2092905 A1 | 8/2009 |
| EP | 2105104 A2 | 9/2009 |
| EP | 1747761 B1 | 10/2009 |
| EP | 1769766 B1 | 2/2010 |
| EP | 2151204 A1 | 2/2010 |
| EP | 2153791 A1 | 2/2010 |
| EP | 2243439 A1 | 10/2010 |
| EP | 1728475 B1 | 8/2011 |
| EP | 2353518 A1 | 8/2011 |
| EP | 2578172 A2 | 4/2013 |
| EP | 2508143 B1 | 2/2014 |
| GB | 2472216 A | 2/2011 |
| JP | H08-229050 A | 9/1996 |
| JP | 2008-018226 | 1/2008 |
| WO | WO 81/03272 A1 | 11/1981 |
| WO | WO 93/07817 A1 | 4/1993 |
| WO | WO 93/22973 A1 | 11/1993 |
| WO | WO 95/10978 A1 | 4/1995 |
| WO | WO 96/35382 A1 | 11/1996 |
| WO | WO 97/10764 A1 | 3/1997 |
| WO | WO 98/00069 A1 | 1/1998 |
| WO | WO 98/40020 A1 | 9/1998 |
| WO | WO 98/57588 A1 | 12/1998 |
| WO | WO 99/23960 A1 | 5/1999 |
| WO | WO 99/40861 A1 | 8/1999 |
| WO | WO 00/24330 A1 | 5/2000 |
| WO | WO 00/24331 A1 | 5/2000 |
| WO | WO 00/25691 A1 | 5/2000 |
| WO | WO 01/28444 A1 | 4/2001 |
| WO | WO 02/080797 A1 | 10/2002 |
| WO | WO 03/001986 A2 | 1/2003 |
| WO | WO 03/013374 A1 | 2/2003 |
| WO | WO 03/020339 A2 | 3/2003 |
| WO | WO 03/028541 A2 | 4/2003 |
| WO | WO 03/030708 A2 | 4/2003 |
| WO | WO 03/068046 A2 | 8/2003 |
| WO | WO 2004/011037 A2 | 2/2004 |
| WO | WO 2004/078051 A2 | 9/2004 |
| WO | WO 2005/052959 A2 | 6/2005 |
| WO | WO 2006/021269 A1 | 3/2006 |
| WO | WO 2006/036706 A1 | 4/2006 |
| WO | WO 2006/055166 A2 | 5/2006 |
| WO | WO 2008/020964 A2 | 2/2008 |
| WO | WO 2008/045348 A2 | 4/2008 |
| WO | WO 2008/099529 A1 | 8/2008 |
| WO | WO 2008/101356 A1 | 8/2008 |
| WO | WO 2009/022614 A1 | 2/2009 |
| WO | WO 2009/036818 A1 | 3/2009 |
| WO | WO 2009/039179 A1 | 3/2009 |
| WO | WO 2009/059741 A1 | 5/2009 |
| WO | WO 2009/082477 A2 | 7/2009 |
| WO | WO 2009/149234 A1 | 12/2009 |
| WO | WO 2010/017266 A1 | 2/2010 |
| WO | WO 2010/104755 A1 | 9/2010 |
| WO | WO 2011/084768 A1 | 7/2011 |
| WO | WO 2011/089717 A1 | 7/2011 |
| WO | WO 2011/144911 A1 | 11/2011 |
| WO | WO 2012/044606 A2 | 4/2012 |
| WO | WO 2013/034629 A1 | 3/2013 |
| WO | WO 2013/062978 A2 | 5/2013 |
| WO | WO 2013/154157 A1 | 10/2013 |
| WO | WO 2015/197395 A8 | 12/2015 |

OTHER PUBLICATIONS

International Search Report for PCT/US2011/036617, Nov. 29, 2011 (9 pages).

International Preliminary Report on Patentability for PCT/US2011/036617, Nov. 20, 2012 (13 pages).

(56) References Cited

OTHER PUBLICATIONS

European Examination Report for Application No. 11722246.3, dated Sep. 24, 2013 (5 pages).
Written Opinion for PCT/US2011/036617, Nov. 29, 2011 (13 pages).
Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Hörmann et al., "Reversible and irreversible denaturation of collagen fibers." Biochemistry, 10, pp. 932-937 (1971).
Henriques. F.C., "Studies in thermal injury V. The predictability and the significance of thermally induced rate processes leading to irreversible epidermal injury." Archives of Pathology, 434, pp. 489-502 (1947).
Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
Chen et al., "Heat-induced changes in the mechanics of a collagenous tissue: pseudoelastic behavior at 37° C," Journal of Biomechanics, 31, pp. 211-216 (1998).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=Ml&sp=1 . . . , accessed Aug. 25, 2009.
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wall et al., "Thermal modification of collagen," J Shoulder Elbow Surg, No. 8, pp. 339-344 (Jul./Aug. 1999).
Wells et al., "Altered Mechanical Behavior of Epicardium Under Isothermal Biaxial Loading," Transactions of the ASME, Journal of Biomechanical Engineering, vol. 126, pp. 492-497 (Aug. 2004).
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Humphrey, J.D., "Continuum Thermomechanics and the Clinical Treatment of Disease and Injury," Appl. Mech. Rev., vol. 56, No. 2 pp. 231-260 (Mar. 2003).
Kurt Gieck & Reiner Gieck, *Engineering Formulas* § Z.7 (7th ed. 1997).
National Semiconductors Temperature Sensor Handbook—http://www.national.com/appinfo/tempsensors/files/temphb.pdf; accessed online: Apr. 1, 2011.
Wright, et al., "Time-Temperature Equivalence of Heat-Induced Changes in Cells and Proteins," Feb. 1998. ASME Journal of Biomechanical Engineering, vol. 120, pp. 22-26.
Covidien Brochure, [Value Analysis Brief], LigaSure Advance™ Pistol Grip, dated Rev. Apr. 2010 (7 pages).
Covidien Brochure, LigaSure Impact™ Instrument LF4318, dated Feb. 2013 (3 pages).
Covidien Brochure, LigaSure Atlas™ Hand Switching Instruments, dated Dec. 2008 (2 pages).
Covidien Brochure, The LigaSure™ 5 mm Blunt Tip Sealer/Divider Family, dated Apr. 2013 (2 pages).
Covidien Brochure, The LigaSure Precise™ Instrument, dated Mar. 2011 (2 pages).
Erbe Electrosurgery VIO®200 S, (2012), p. 7, 12 pages, accessed Mar. 31, 2014 at http://www.erbe-med.com/erbe/media/Marketingmaterialien/85140-170_ERBE_EN_VIO_200_S_D027541.
Jang, J. et al. "Neuro-fuzzy and Soft Computing." Prentice Hall, 1997, pp. 13-89, 199-293, 335-393,453-496, 535-549.
Douglas, S.C. "Introduction to Adaptive Filter". Digital Signal Processing Handbook. Ed. Vijay K. Madisetti and Douglas B. Williams. Boca Raton: CRC Press LLC, 1999.
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Sullivan, "Optimal Choice for Number of Strands in a Litz-Wire Transformer Winding," IEEE Transactions on Power Electronics, vol. 14, No. 2, Mar. 1999, pp. 283-291.

* cited by examiner

SURGICAL INSTRUMENTS AND END EFFECTORS THEREFOR

CROSS-REFERENCE TO RELATED APPLICATION

This application is a continuation application claiming priority under 35 U.S.C. §120 to U.S. patent application Ser. No. 12/781,243, entitled SURGICAL INSTRUMENTS AND END EFFECTORS THEREFOR, filed May 17, 2010, U.S. Pat. No. 8,685,020, the entire disclosure of which is hereby incorporated by reference herein.

BACKGROUND

Various embodiments are directed to surgical instruments that may be used, for example, in open and minimally invasive surgical environments.

In various circumstances, a surgical instrument can be configured to apply energy to tissue in order to treat and/or destroy the tissue. In certain circumstances, a surgical instrument can comprise one or more electrodes which can be positioned against and/or positioned relative to the tissue such that electrical current can flow from one electrode, through the tissue, and to the other electrode. The surgical instrument can comprise an electrical input, a supply conductor electrically coupled with the electrodes, and/or a return conductor which can be configured to allow current to flow from the electrical input, through the supply conductor, through the electrodes and the tissue, and then through the return conductor to an electrical output, for example. Alternatively, the surgical instrument can comprise an electrical input, a supply conductor electrically coupled with the electrodes, and/or a return conductor which can be configured to allow current to flow from the electrical input, through the supply conductor, through the active electrode and the tissue, and to the return electrode through the return conductor to an electrical output. In various circumstances, heat can be generated by the current flowing through the tissue, wherein the heat can cause one or more hemostatic seals to form within the tissue and/or between tissues. Such embodiments may be particularly useful for sealing blood vessels, for example. The surgical instrument can also comprise a cutting member that can be moved relative to the tissue and the electrodes in order to transect the tissue.

By way of example, energy applied by a surgical instrument may be in the form of radio frequency ("RF") energy. RF energy is a form of electrical energy that may be in the frequency range of 300 kilohertz (kHz) to 1 megahertz (MHz). In application, RF surgical instruments transmit low frequency radio waves through electrodes, which cause ionic agitation, or friction, in effect resistive heating, increasing the temperature of the tissue. Since a sharp boundary is created between the affected tissue and that surrounding it, surgeons can operate with a high level of precision and control, without much sacrifice to the adjacent normal tissue. The low operating temperatures of RF energy enables surgeons to remove, shrink or sculpt soft tissue while simultaneously sealing blood vessels. RF energy works particularly well on connective tissue, which is primarily comprised of collagen and shrinks when contacted by heat.

Further, in various open and laparoscopic surgeries, it is necessary to coagulate, seal or fuse tissues. One preferred means of tissue-sealing relies upon the application of electrical energy to captured tissue to cause thermal effects therein for sealing purposes. Various monopolar and bi-polar RF jaw structures have been developed for such purposes. In general, the delivery of RF energy to a captured tissue volume elevates the tissue temperature and thereby at least partially denatures proteins in the tissue. Such proteins, including collagen, are denatured into a pertinacious amalgam that intermixes and fuses together as the proteins denature or form new cross links. As the treated region heals over time, this biological "weld" is reabsorbed by the body's wound healing process.

In a typical arrangement of a bi-polar radiofrequency (RF) jaw, the face of each jaw comprises an electrode. RF current flows across the captured tissue between electrodes in opposing jaws. Most commercially available bi-polar jaws provide a low tissue strength weld immediately post-treatment.

During some procedures, it is often necessary to access target tissue that requires severe manipulation of the end effector. In such applications, it would be desirable to have a curved and/or articulatable end effector arrangement to improve access and visualization of the surgical area by the surgeon.

The foregoing discussion is intended only to illustrate various aspects of the related art in the field of the invention at the time, and should not be taken as a disavowal of claim scope.

SUMMARY

In various embodiments, a surgical instrument is provided. The surgical instrument comprises an elongate shaft and an end effector extending from the elongate shaft, the end effector comprising a first member and a second member, wherein the first member is movable relative to the second member to transition the end effector between an open configuration and an approximated configuration to clamp tissue between the first member and the second member. The surgical instrument further comprises a camming assembly movable along a curved path, the camming assembly comprising a first camming member, wherein the first camming member comprises a first distal camming portion, a first proximal camming portion, and a first flexible portion extending between the first distal camming portion and the first proximal camming portion. The camming assembly further comprises a second camming member, wherein the second camming member comprises a second distal camming portion, a second proximal camming portion, and a second flexible portion extending between the second distal camming portion and the second proximal camming portion. The camming assembly further comprises a connector at least partially disposed between the first camming member and the second camming member, wherein the connector comprises a cutting member at a distal portion thereof, and wherein the camming assembly is movable relative to the end effector to exert a camming force against the first member and the second member to transition the end effector to the approximated configuration.

In various embodiments, a surgical instrument is provided. The surgical instrument comprises an elongate shaft, an end effector extending from the elongate shaft, the end effector comprising a first jaw and a second jaw, wherein the first jaw is movable relative to the second jaw to transition the end effector between an open configuration and an approximated configuration to clamp tissue between the first jaw and the second jaw. The surgical instrument further comprises a bendable firing member movable along a non-linear path, the bendable firing member comprising a first bendable portion defining a first plane, the first bendable portion comprising a first camming surface at a distal portion thereof, a second bendable portion defining a second plane, the second bendable portion comprising a second camming surface at a distal portion thereof, and a connector defining a third plane intersecting the first plane and the second plane, wherein the connector comprises a cutting member at a distal portion thereof, and wherein the first camming surface and the second camming surface are configured to engage the first jaw and the second jaw respectively to transition the end effector to the approximated configuration.

In various embodiments, an end effector for use with a surgical instrument is provided. The end effector comprises a first jaw, a second jaw, wherein the first jaw is movable relative to the second jaw to transition the end effector between an open configuration and an approximated configuration to clamp tissue between the first jaw and the second jaw, and a camming assembly movable along a curved path. The camming assembly comprises a first camming member, wherein the first camming member comprises a first distal camming portion, a first proximal camming portion, and a first flexible portion extending between the first distal camming portion and the first proximal camming portion. The camming assembly further comprises, one, a second camming member and, two, a connector at least partially disposed between the first camming member and the second camming member, wherein the connector comprises a cutting member at a distal portion thereof, and wherein the camming assembly is movable relative to the end effector to exert a camming force against the first jaw and the second jaw to transition the end effector to the approximated configuration.

BRIEF DESCRIPTION OF THE DRAWINGS

Various features of the embodiments described herein are set forth with particularity in the appended claims. The various embodiments, however, both as to organization and methods of operation, together with advantages thereof, may be understood in accordance with the following description taken in conjunction with the accompanying drawings as follows.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
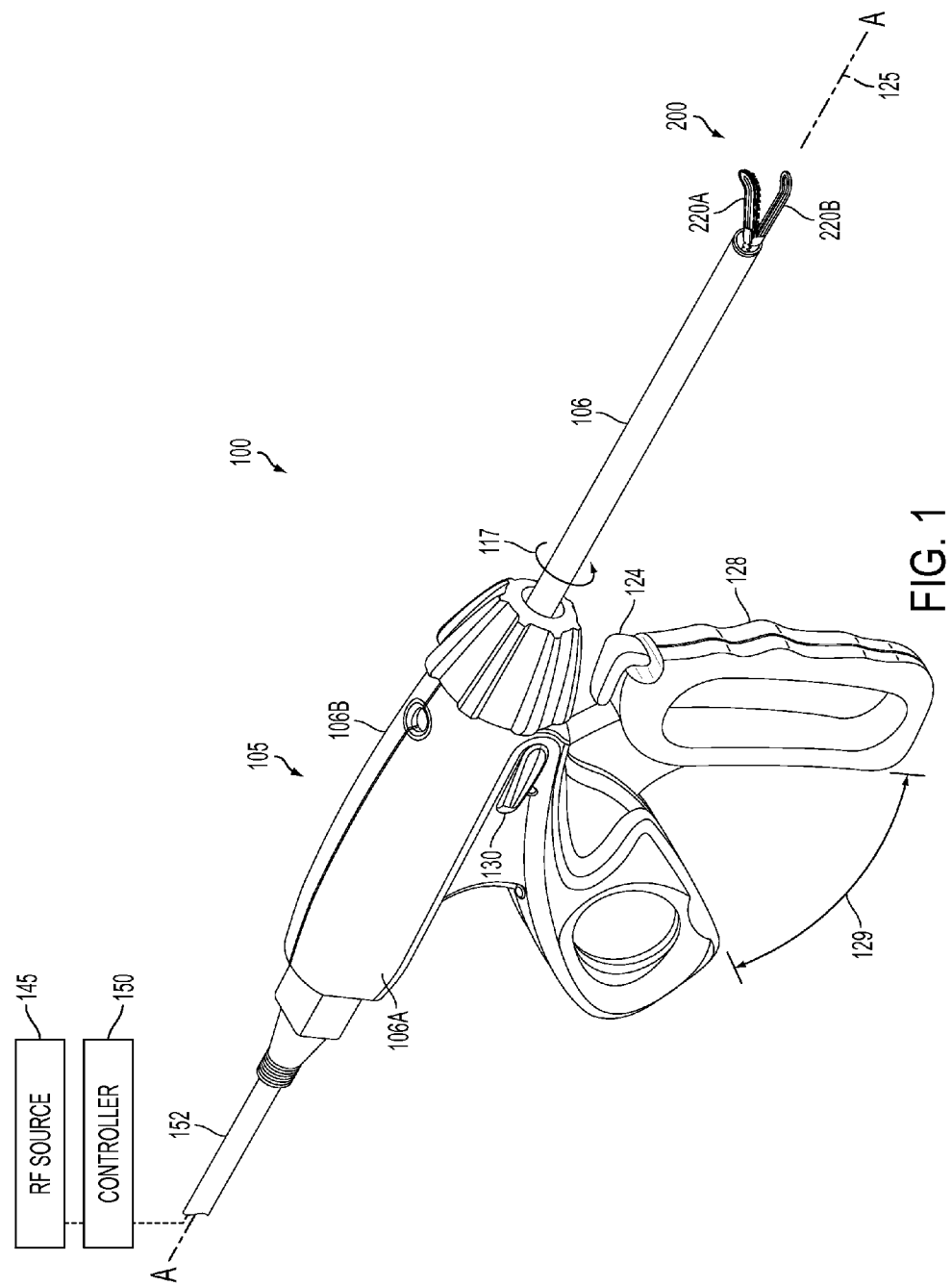
FIG. 1 is a perspective view of an electrosurgical instrument according to one non-limiting embodiment of the present invention.

Various embodiments are directed to apparatuses, systems, and methods for the treatment of tissue. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and illustrative. Variations and changes thereto may be made without departing from the scope of the claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Various embodiments of systems and methods of the invention relate to creating thermal "welds" or "fusion" within native tissue volumes. The alternative terms of tissue "welding" and tissue "fusion" may be used interchangeably herein to describe thermal treatments of a targeted tissue volume that result in a substantially uniform fused-together tissue mass, for example, in welding blood vessels that exhibit substantial burst strength immediately post-treatment. The strength of such welds is particularly useful for (I) permanently sealing blood vessels in vessel transaction procedures; (ii) welding organ margins in resection procedures; (iii) welding other anatomic ducts wherein permanent closure is required; and also (iv) for performing vessel anastomosis, vessel closure or other procedures that join together anatomic structures or portions thereof. The welding or fusion of tissue as disclosed herein is to be distinguished from "coagulation", "hemostasis" and other similar descriptive terms that generally relate to the occlusion of blood flow within small blood vessels or vascular zed tissue. For example, any surface application of thermal energy can cause coagulation or hemostasis—but does not fall into the category of "welding" as the term is used herein. Such surface coagulation does not create a weld that provides any substantial strength in the treated tissue.

At the molecular level, the phenomena of truly "welding" tissue as disclosed herein may result from the thermally-induced penetration of collagen and other protein molecules in a targeted tissue volume to create a transient liquid or gel-like pertinacious amalgam. A selected energy density is provided in the targeted tissue to cause hydrothermal breakdown of intra- and intermolecular hydrogen crosslink's in collagen and other proteins. The denatured amalgam is maintained at a selected level of hydration—without desiccation—for a selected time interval which can be very brief. The targeted tissue volume is maintained under a selected very high level of mechanical compression to ensure that the unwound strands of the denatured proteins are in close proximity to allow their intertwining and entanglement. Upon thermal relaxation, the intermixed amalgam results in protein entanglement as re-cross linking or repatriation occurs to thereby cause a uniform fused-together mass.

Various embodiments disclosed herein provide electrosurgical jaw structures adapted for transecting captured tissue between the jaws and for contemporaneously welding the captured tissue margins with controlled application of RF energy. The jaw structures of certain embodiments can comprise first and second opposing jaws that carry positive temperature coefficient (PTC) or resistance bodies for modulating RF energy delivery to the engaged tissue.

FIG. 1 shows an electrosurgical instrument 100 according to a non-limiting embodiment of the invention. Electrosurgical instrument 100 comprises a proximal handle 105, a distal end effector 200, and an introducer or elongate shaft member 106 disposed in-between. In various embodiments, end effector 200 comprises a set of operable-closeable jaws 220A and 220B. The end effector 200 may be adapted for capturing, welding, and transecting tissue, for example. First jaw 220A and second jaw 220B may close to thereby capture or engage tissue therebetween. First jaw 220A and second jaw 220B may also apply compression to the tissue. In alternative embodiments, the end effector may be comprised of one or two movable jaws.

Figure 2:
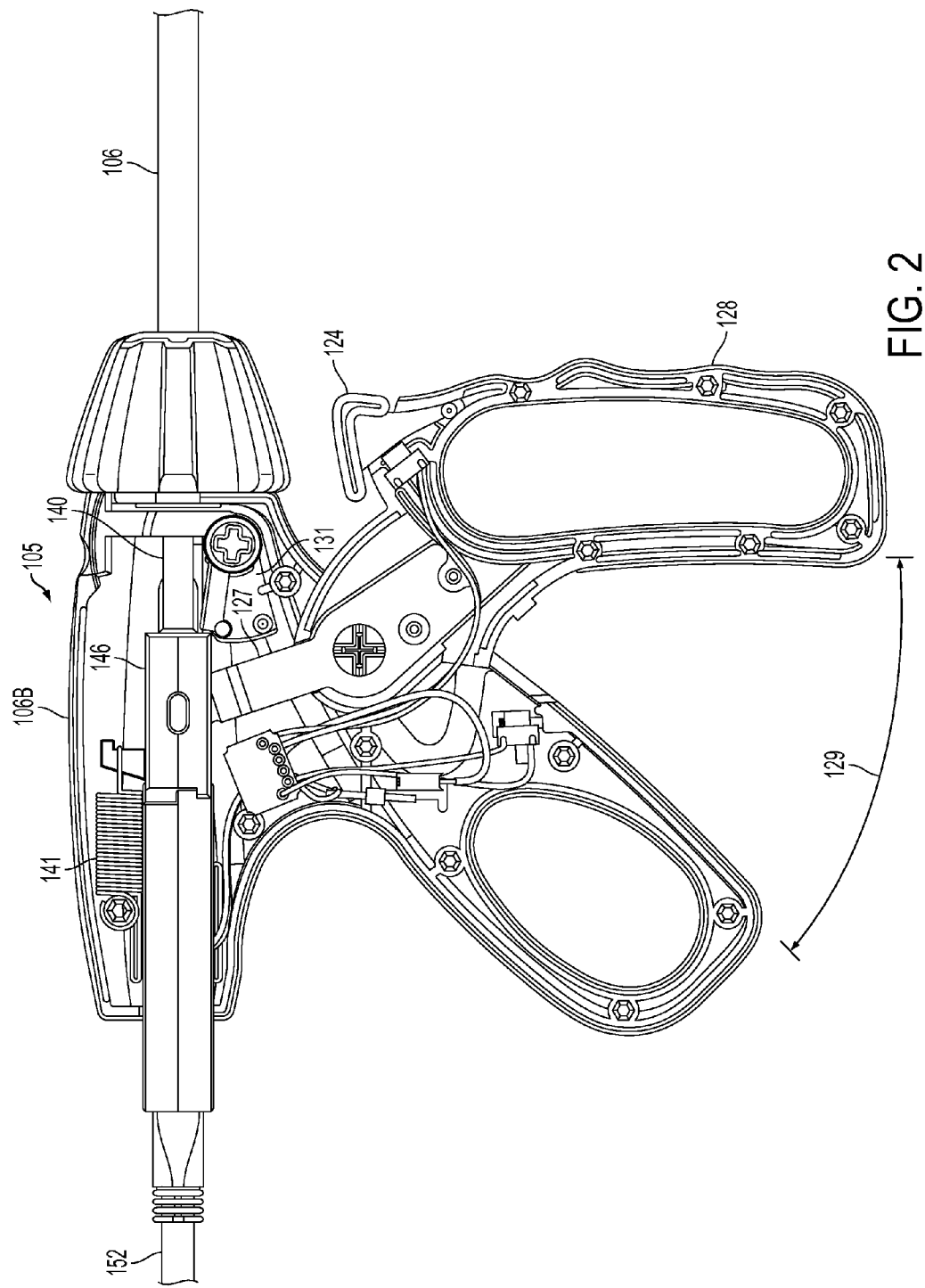
FIG. 2 is a side view of the handle depicted in FIG. 1 with a portion of the housing thereof omitted to illustrate various handle components.

Moving now to FIG. 2, a side view of the handle 105 is shown with half of a first handle body 106A (see FIG. 1) being removed to illustrate some of the components within second handle body 106B. Handle 105 may comprise a lever arm 128 which may be pulled along a path 129. Lever arm 128 may be coupled to a translatable member 140 that is disposed within the elongate shaft 106 by a shuttle 146 that is operably engaged to an extension 127 of lever arm 128. The shuttle 146 may further be connected to a biasing device, such as spring 141. The spring 141 may also be connected to the second handle body 106B, to bias the shuttle 146 and thus the translatable member 140 in a proximal direction, thereby urging the jaws 220A and 220B to an open position as seen in FIG. 1. Also, referring to FIGS. 1 and 2, a locking member 131 (see FIG. 2) may be moved by a locking switch 130 (see FIG. 1) between a locked position, where the shuttle 146 is substantially prevented from moving distally as illustrated, and an unlocked position, where the shuttle 146 may be allowed to freely move in the distal direction, toward the elongate shaft 106. The handle 105 can be any type of pistol-grip or other type of handle known in the art that is configured to carry actuator levers, triggers or sliders for actuating the first jaw 220A and second jaw 220B. Elongate shaft 106 may have a cylindrical or rectangular cross-section and can comprise a thin-wall tubular sleeve that extends from handle 105. Elongate shaft 106 may have a bore extending therethrough for carrying actuator mechanisms such as, for example, translatable member 140, for actuating the jaws 220A, 220B and for carrying electrical leads for delivery of electrical energy to electrosurgical components of end effector 200.

The elongate shaft member 106 along with first jaw 220A and second jaw 220B may, in some embodiments, be continuously rotatable in either a clockwise or counterclockwise direction, as shown by arrow 117 (FIG. 1), relative to handle 105 through, for example, a rotary triple contact. First jaw 220A and second jaw 220B can remain operable-closeable and openable while being rotated. First jaw 220A and second jaw 220B may be coupled to the electrical source 145 and controller 150 through electrical leads in cable 152 to function as paired bi-polar electrodes with a positive polarity (+) and a negative polarity (−) or alternatively monopolar electrodes with positive (+) polarity and a remote grounding pad with a negative (−) polarity.

Figure 4:
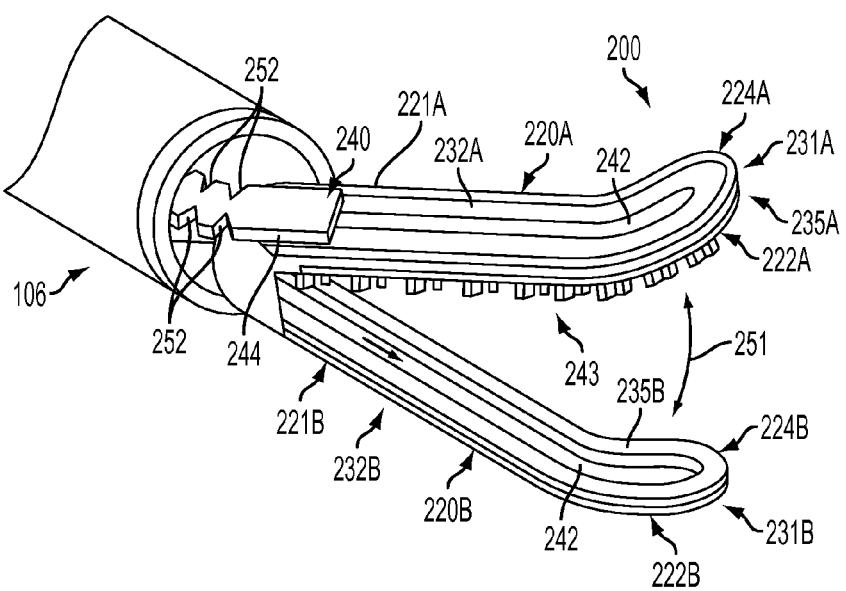
FIG. 4 is a partial perspective view of the end effector embodiment depicted in FIG. 3 in an open position.

The first jaw 220A may have a first elongate portion 221A that is pivotally coupled to a second elongate portion 221B of the second jaw 220B by, for example, pins, grunions, or other known attachment arrangement such that the first jaw 220A may be pivoted toward and away from the second jaw 220B as represented by arrow 251 in FIG. 4. Further, the first jaw 220A and second jaw 220B may each have tissue-gripping elements, such as teeth 243, disposed on the inner portions of first jaw 220A and second jaw 220B. First jaw 220A may comprise a first jaw body 231A with a first outward-facing surface 232A and a first energy delivery surface 235A. Second jaw 220B may comprise a second jaw body 231B with a second outward-facing surface 232B and a second energy delivery surface 235B. First energy delivery surface 235A and second energy delivery surface 235B may, for example, both extend in a "U" shape about the distal end of working end 200.

Figure 3:
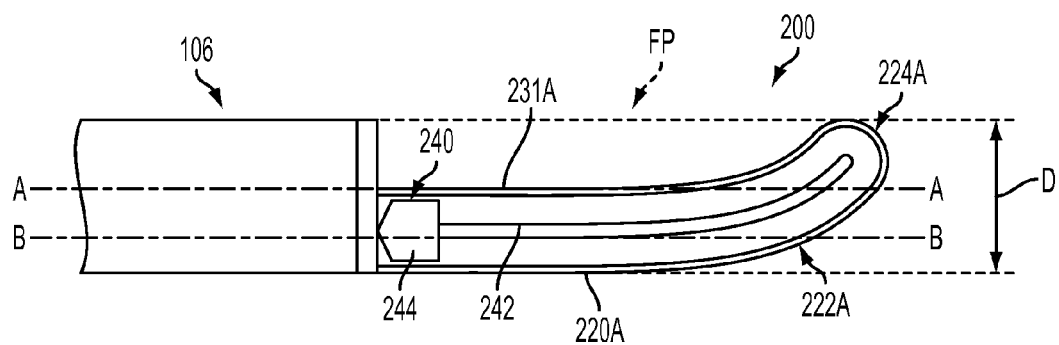
FIG. 3 is a top view of an end effector according to one non-limiting embodiment of the present invention.

As can be seen in FIGS. 1 and 3, the elongate shaft 106 defines a first longitudinal axis A-A. In various non-limiting embodiments, the first and second elongate portions 221A, 221B of the first and second jaws 220A, 220B, respectively are aligned along a second axis B-B that is offset from the first axis A-A. As can be further seen in FIG. 4, the first jaw body 231A may have a curved distal portion 222A and the second jaw body 231B may have a curved distal portion 222B. FIG. 3 is a top view of the end effector 200 and illustrates an embodiment wherein the first jaw 220A and the second jaw 220B have substantially matching shapes. As used herein, the terms "substantially" and "substantially the same" refer to characteristics or components that are otherwise identical, but for the normal manufacturing tolerances commonly experienced when manufacturing such components. As can be further seen in FIG. 3, the distal tip portion 224A of the jaw body 231A as well as the distal tip portion 224B of the second jaw body 231B are preferably located within the diameter "D" or "footprint FP" (for elongate shafts 106 that do not have a circular cross-sectional shape) of the elongate shaft 106 such that the end effector 200 may be inserted through an opening that can accommodate the elongate shaft 106. The offset nature of the end effector 200 enables the jaws 220A, 220B to be provided with a curved or irregular portion that is curved relatively sharper than other jaw embodiments wherein the jaws are axially aligned with the elongate shaft 106. It will be understood that the jaws 220A, 220B may have various curved portions, provided that no portion of the jaws 220A, 220B protrude laterally outward beyond the diameter "D" or footprint FP of the elongate shaft 106 for a distance that might otherwise prevent the insertion through a lumen such as, for example, a trocar or the like unless it is deflectable thereby allowing insertion through such a lumen.

Figure 5:
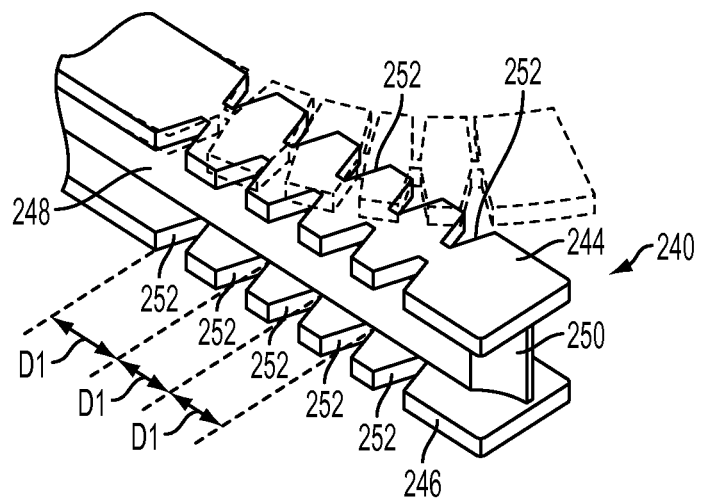
FIG. 5 is a partial perspective view of a portion of a translatable member according to one non-limiting embodiment of the present invention with an alternative flexed position shown in phantom.

FIGS. 3-5 show a portion of translatable, reciprocating member or reciprocating "I-beam" member 240. The lever arm 128 of handle 105 may be adapted to actuate translatable member 240 which also functions as a jaw-closing mechanism. For example, translatable member 240 may be urged distally as lever arm 128 is pulled proximally along path 129. The distal end of translatable member 240 comprises a flanged "I"-beam that is configured to slide within slots 242 in jaws 220A and 220B. See FIG. 4. Translatable member 240 slides within slots 242 to open and close first jaw 220A and second jaw 220B. As can be most particularly seen in FIG. 5, the distal end of translatable member 240 comprises an upper flange 244 and a lower flange 246 that are separated by a web portion 248 that has a sharpened distal end 250 for cutting tissue. In various embodiments, the translatable member 240 may be fabricated from, for example, stainless steel or similar elastic materials or alternatively from the class of superelastic materials such as Nitinol or the like. In various embodiments, the upper flange 244 and the lower flange 246 of translatable member 240 may each be optionally provided with cutout portions 252. The cutouts 252 may be substantially V-shaped with their narrowest portion adjacent the web 248 and their widest portion opening at the lateral edge of the flange as shown in FIG. 5. The cutouts 252 in the upper flange 244 may be substantially aligned with like cutouts 252 in the lower flange 246. To facilitate relatively tight bending of the translatable member 240 (as illustrated in phantom lines in FIG. 5), the cutouts 252 may be oriented relatively close together. Such translatable member arrangements enable the translatable member to flex around the curved slots 242 in the first and second jaws 220A, 220B. Thus, as the translatable member 240 is advanced distally by actuating the lever 128, the upper and lower flanged portions 244, 246 engage the first jaw 220A and the second jaw 220B to cam the jaws 220A, 220B together to clamp and cut tissue therebetween.

Figure 6:
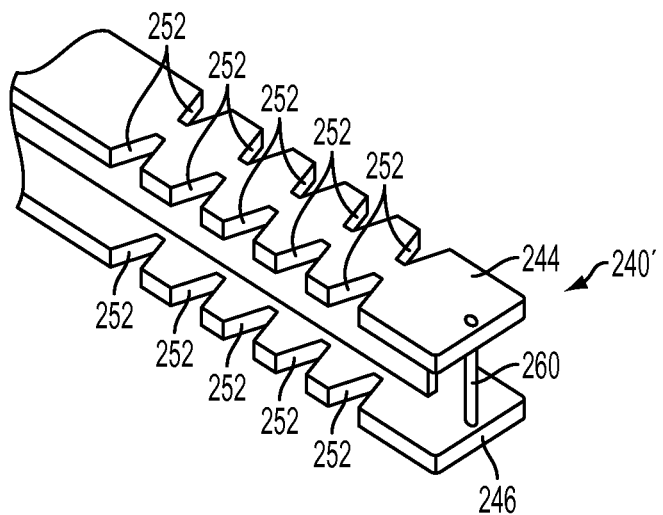
FIG. 6 is a perspective view of a portion of a translatable member according to another non-limiting embodiment of the present invention.

FIG. 6 illustrates another translatable member 240' that is similar to translatable member 240 described above, except that a tissue-cutting wire 260 is provided between the upper and lower flanges for tissue cutting purposes. The wire 260 may be fabricated from, for example, stainless steel or the like and be mounted in tension between the upper flange 244 and the lower flange 246. The wire 260 may also be used in connection with a translatable member 240 that does not have the cutouts 252 in its flanges 244, 246. In an alternative embodiment, the wire 260 may be connected to the RF power source either directly or indirectly to cut electrically.

Figure 7:
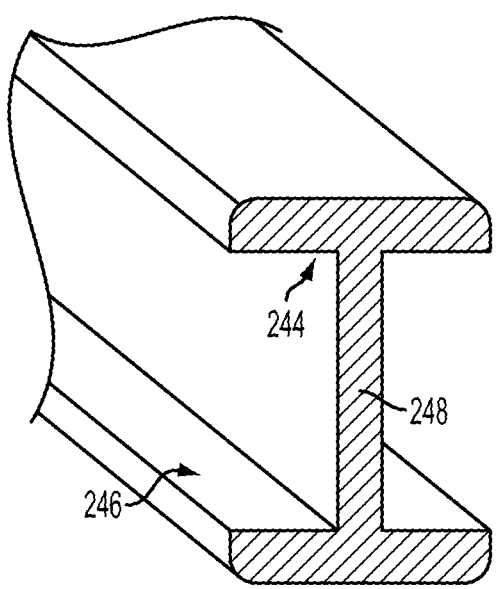
FIG. 7 is a partial cross-sectional perspective view of a translatable member according to another non-limiting embodiment of the present invention.
Figure 8:
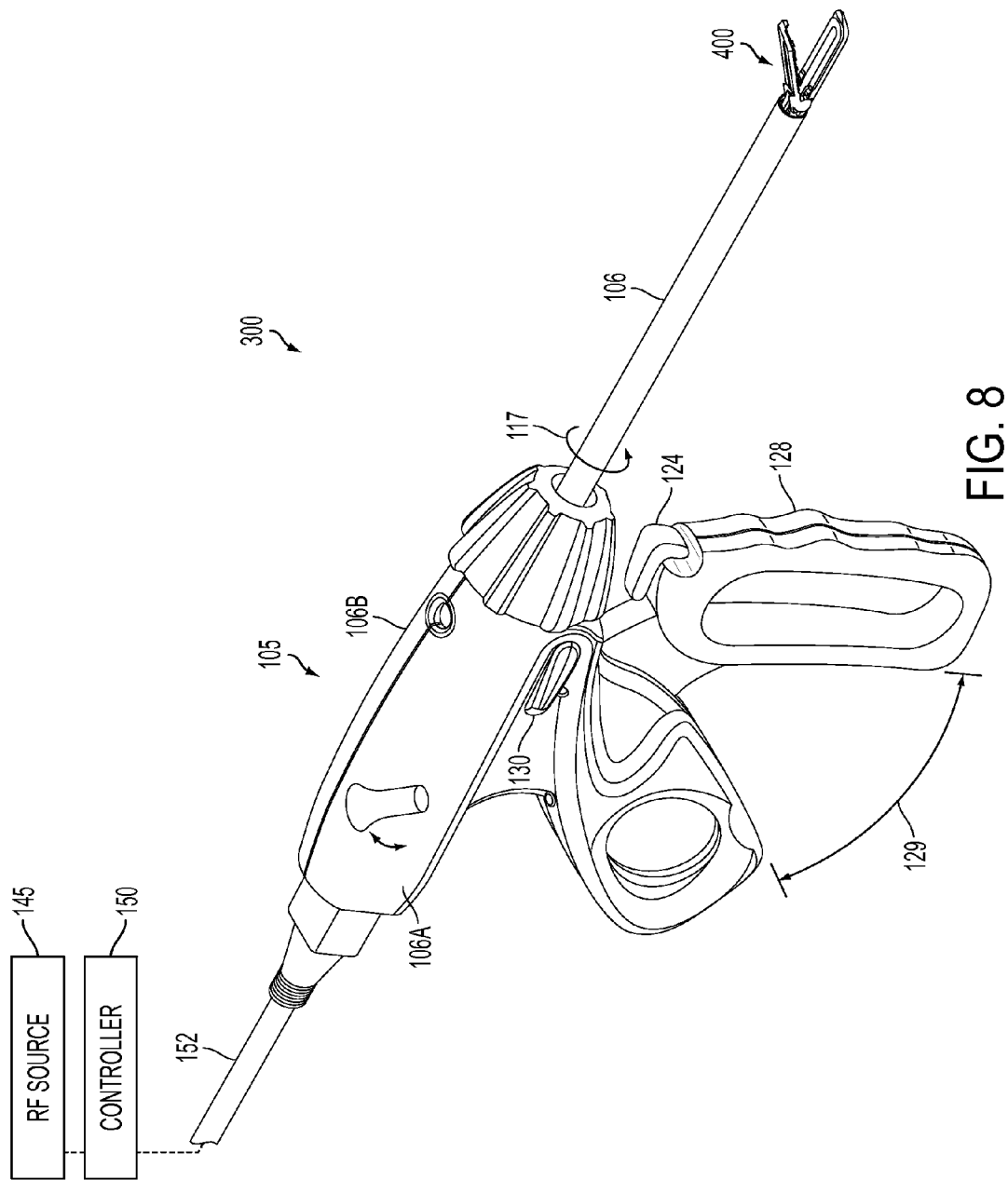
FIG. 8 is a perspective view of an electrosurgical instrument according to another non-limiting embodiment of the present invention.

In various embodiments, the translatable member 240 may be provided with the cut outs 252 as described above and be fabricated from, for example, a relatively flexible or super elastic material or alloy such as Nitinol, NiTi or other alloys with similar properties. In other embodiments, the translatable member may be fabricated out of Nitinol, NiTi or similar material and have the shape of an I-beam without the cut outs 252 in the flanges. See FIG. 7.

Figure 9:
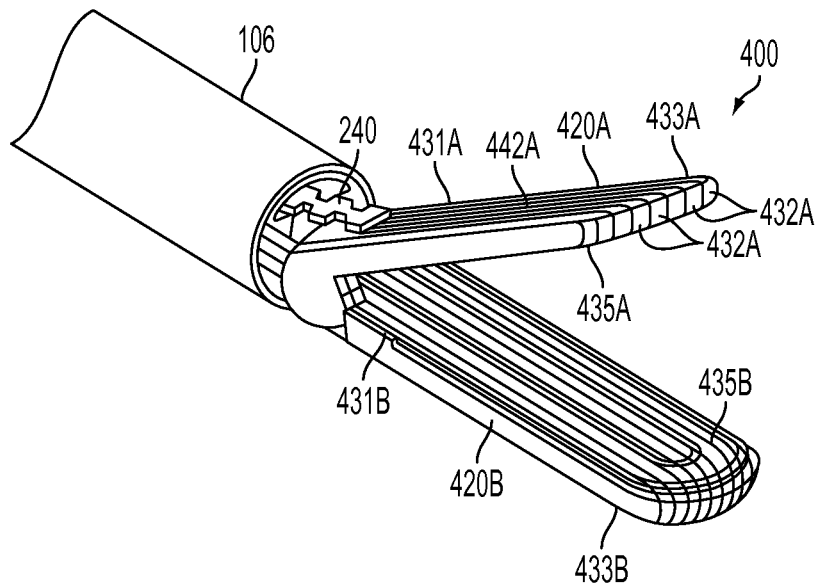
FIG. 9 is a partial perspective view of an end effector of another non-limiting embodiment of the present invention in an open position.
Figure 10:
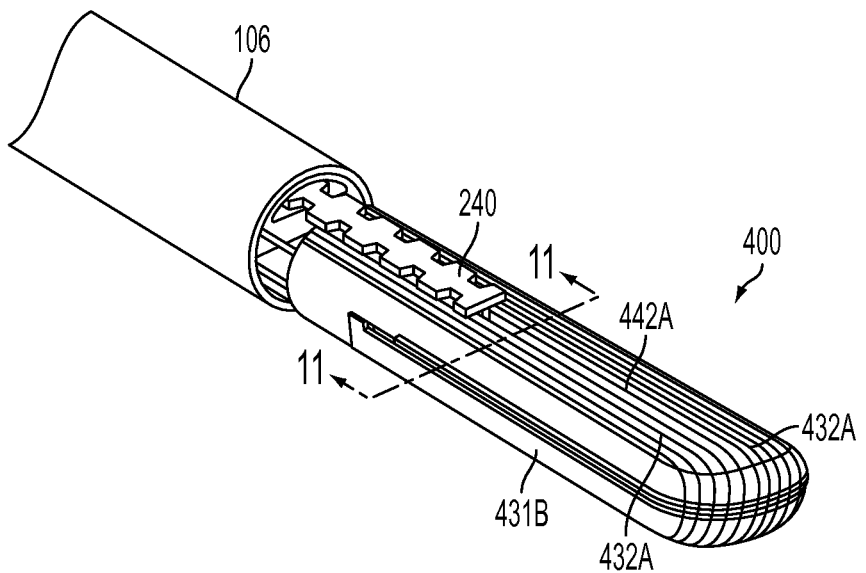
FIG. 10 is another partial perspective view of the end effector of FIG. 9 in a closed position.

FIGS. 8-11 illustrate another electrosurgical instrument 300 that employs another non-limiting end effector embodiment 400 of the present invention. The electrosurgical instrument 300 may be identical in construction and operation as electrical surgical instrument 100 except for the differences noted below. Turning to FIGS. 9 and 10, it can be seen that the end effector 400 includes a first jaw 420A and a second jaw 420B. The first jaw 420A may be pivotally coupled to the second jaw 420B to enable the first jaw 420A to pivot between an open position (FIG. 9) and a closed position (FIG. 10). First jaw 420A may comprise an upper first jaw body 431A that is formed from a series of vertically laminated layers 432A of material. In various embodiments, the laminated layers 432A may be fabricated from materials that comprise a thermal and/or electrical insulator, for example, zirconium, partially stabilized zirconium, aluminum oxide, silicon nitride, alumina-chromic, hydroxyapatite, other non-conductive glass materials, or other non-conductive ceramic materials. Other non-conductive glass-ceramic materials may also be employed. The layers 432A may be vertically laminated together by an electrometric material 434A such as, for example, polyisoprene, silicone, etc. See FIG. 11. The laminated layers 432A may serve to define a slot 442A for accommodating a translatable member 240 or 240' in the manner described above. The first jaw body 431A has an upper first outward-facing surface 433A and an upper first energy delivery surface 435A. As used herein, the term "vertically laminated" means that the layers of material extend perpendicular to a plane along with the energy delivery surface lies. Second jaw 420B may comprise a lower second jaw body 431B that is formed from another series of vertically laminated layers 432B that may be fabricated and laminated from the various materials described above. The second jaw body 431B may have a lower second outward-facing surface 433B and a lower second energy delivery surface 435B. First energy delivery surface 435A and second energy delivery surface 435B may both extend in a "U" shape about the distal end of the end effector 200.

Figure 11:
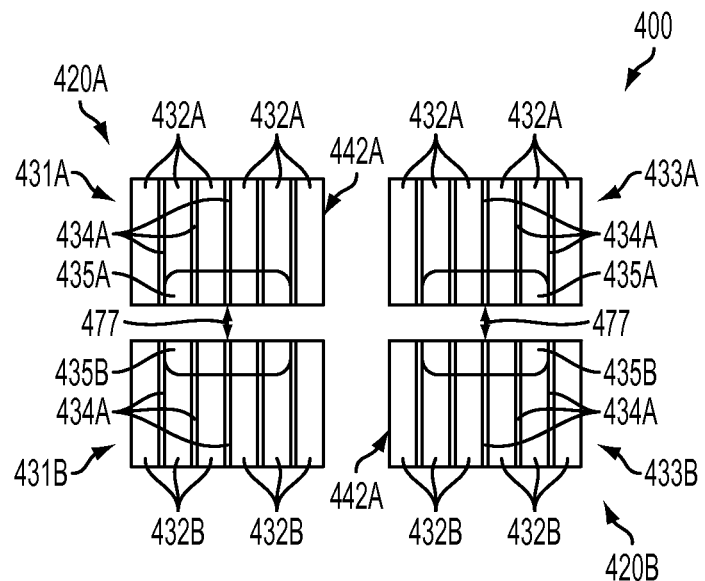
FIG. 11 is a cross-sectional view of the end effector of FIG. 10 taken along line 11-11 in FIG. 10.

As seen in FIG. 11, electrosurgical energy may be delivered through current paths 477 between first energy delivery surface 435A and second energy delivery surface 435B. Translatable member 240 may comprise an insulating layer to prevent member 240 from functioning as a conductive path for current delivery. Opposing first and second energy delivery surfaces 435A and 435B may carry variable resistive positive temperature coefficient (PTC) bodies or matrices that are coupled to electrical source 145 and controller 150 in series and parallel circuit components. First energy delivery surface 435A and the corresponding PTC body can have a negative polarity (−) while second energy delivery surface 435B and the corresponding PTC body can have a positive polarity (+). PTC materials will "trip" and become highly resistive or non-conductive once a selected trip temperature is exceeded. First energy delivery surface 435A and second energy delivery surface 435B can carry any of the PTC matrix and electrode components disclosed in U.S. Pat. No. 6,929,644 entitled ELECTROSURGICAL JAW STRUCTURE FOR CONTROLLED ENERGY DELIVERY and U.S. Pat. No. 6,770,072 entitled ELECTROSURGICAL JAW STRUCTURE FOR CONTROLLED ENERGY DELIVERY, the respective disclosures of which are each fully incorporated herein by reference. The use of PTC materials in electrosurgical instruments is also described in U.S. Pat. No. 7,112,201 entitled ELECTROSURGICAL JAW STRUCTURE FOR CONTROLLED ENERGY DELIVERY, U.S. Pat. No. 6,929,622 entitled ELECTROSURGICAL JAW STRUCTURE FOR CONTROLLED ENERGY DELIVERY, and U.S. Patent Application Publication No. 2010/0036370A1 entitled ELECTROSURGICAL INSTRUMENT JAW STRUCTURE WITH CUTTING TIP, the respective disclosures of which are each fully incorporated herein by reference. In various embodiments, however, the first energy delivery surface 435A and the second energy delivery surface 435B are each fabricated from layers that are laminated together by, for example, adhesive or mechanical means.

Figure 12:
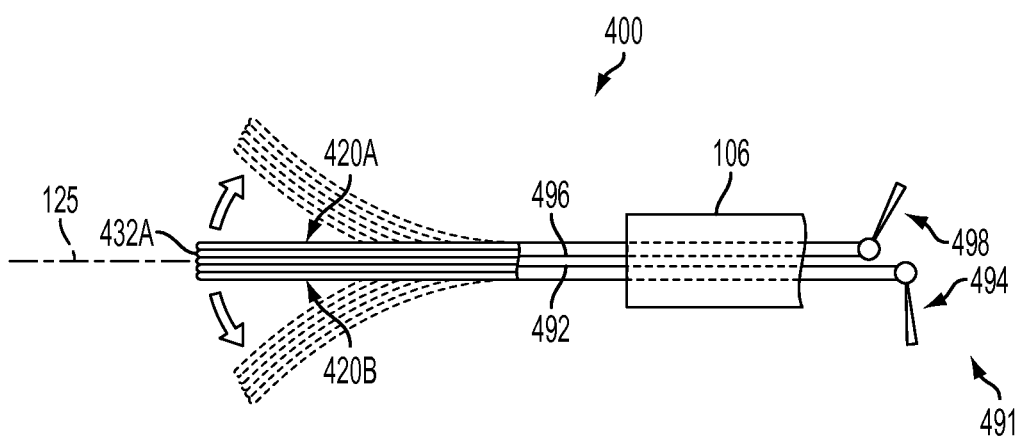
FIG. 12 is a top diagrammatical view of the end effector of FIGS. 9 and 10 with alternative flexed positions being shown in phantom.
Figure 13:
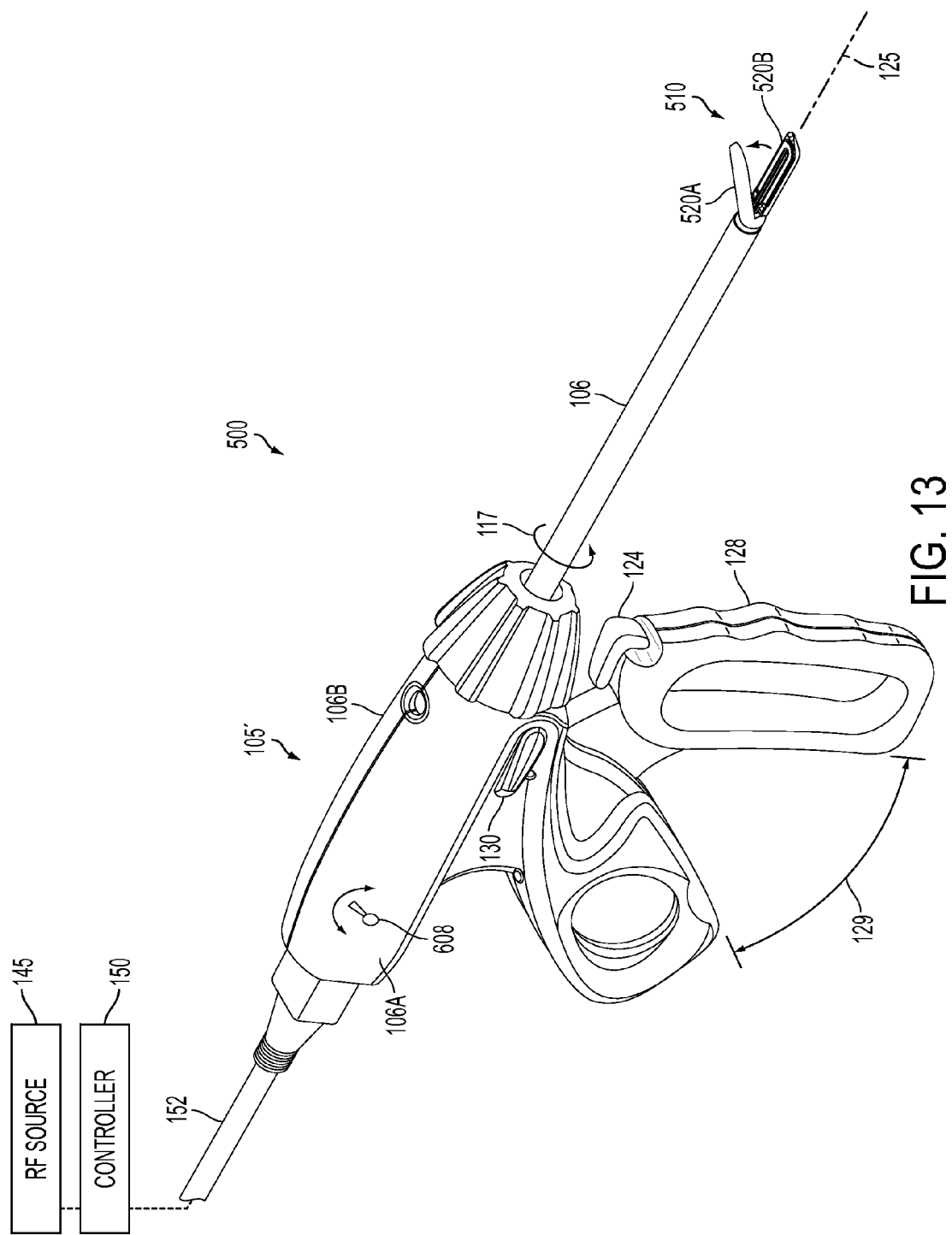
FIG. 13 is a perspective view of an electrosurgical instrument according to another non-limiting embodiment of the present invention.
Figure 14:
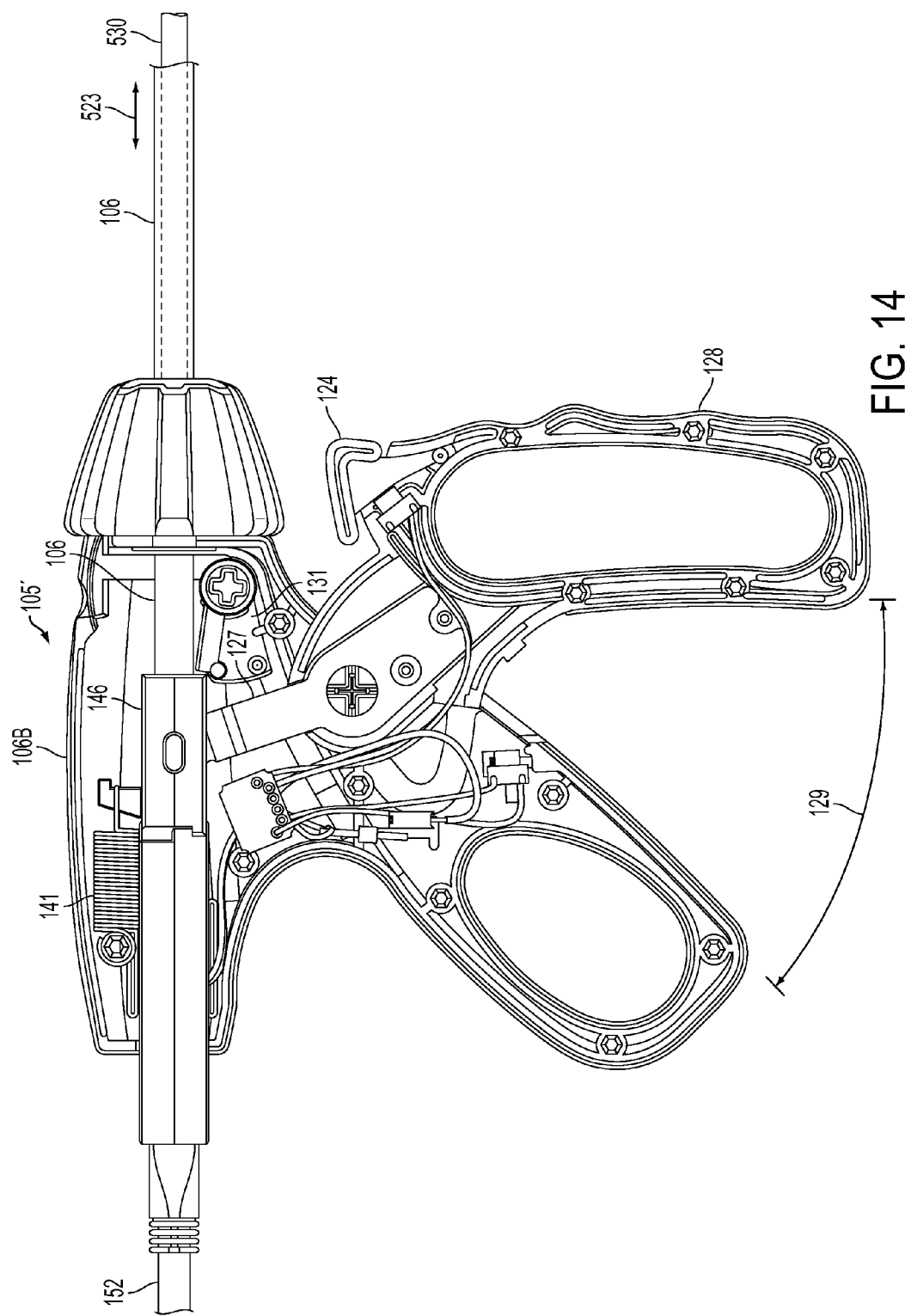
FIG. 14 is a side view of the handle depicted in FIG. 13 with a portion of the housing thereof omitted to illustrate various handle components.

FIG. 12 is a top diagrammatical view of the end effector 400 and an actuating system 491 that may be employed to flex the end effector 400 between the three positions illustrated therein. As can be seen in that Figure, the actuating system 491 may comprise at least one "first" cable 492 attached to each of said first and second jaws 420A, 420B. That is at least one first cable 492 is attached to the first jaw 420A and at least one other first cable 492 is attached to the second jaw 420B. Likewise, at least one "second" cable 496 is attached to each of the first jaw 420A and the second jaw 420B. That is, at least one second cable 496 is attached to the first jaw 420A and at least one other second cable 496 is attached to the second jaw 420B. Such actuation system 491 enables the clinician to "pull" portions of the first jaw 420A and portions of the second jaw 420B out of axial alignment with the elongate shaft 106. That is, for example, the first cables 492 may be used to pull portions of the first and second jaws 420A, 420B to the left of axis 125 and the second cables 496 may be used to pull portions of the first and second jaws 420A, 420B to the right of the axis 125. The first cables 492 may extend through the hollow elongated shaft 106 to be coupled to a first actuation member 494 that is operably supported by the handle 105. See FIG. 12. Similarly, the second cables 496 may extend through the hollow elongated shaft 106 to be coupled to a left actuation member 498 that is operably supported by the handle 105. For example, each actuation member 494, 498 may comprise a lever arm, button, etc. that is movably supported on the handle 105 and coupled to the corresponding cables 492, 496 such that movement of the actuation member 494 in one direction applies tension to the cables 492 to cause the end effector to flex to one side of axis 125. Movement of the actuation members 494, 498 in other directions permits the cables 492, 496 to assume positions wherein the end effector 400 can assume a relatively coaxial orientation with the elongated shaft member 106 to permit insertion of the end effector 400 through a lumen that will accept the hollow elongated shaft member 106. Similarly, movement of the actuation member 498 in one direction applies tension to the cables 496 to flex the end effector 400 to another side of axis 125. The actuation members 494, 498 may be selectively lockable in the various positions using known locking arrangements. In still other embodiments, one or more motors may be employed to apply tension to and relieve tension from the cables to effectuate a desired flexing or bending of the end effector 400. It will be understood that the end effector 400 may otherwise operate in the various manners disclosed herein and that the unique and novel design of the translatable member 240 or 240' may flex or bend to travel through the respective slots 442A, 442B.

FIGS. 13-17 illustrate an electrosurgical instrument 500 according to another non-limiting embodiment of the present invention. This embodiment may employ a handle 105' that is somewhat similar to handle 105 described above. However, the electrosurgical instrument 500 does not employ a translatable member that is designed to cut tissue and close the jaws 520A and 520B of the end effector 510. In this embodiment, the second jaw 520B is coupled to a spine member 530 that extends through the hollow elongate tube 106 and is attached to the handle 105'. The proximal end of the hollow elongate tube 106 interfaces with a shuttle member 146 that is movably supported in handle 105' and interfaces with the lever 128 such that pivotal movement of the lever arm 128 along path 129 will cause the shuttle 146 and elongate tube 106 to move axially relative to the handle 105' and the spine member 530 as represented by arrow 523. See FIGS. 14 and 15. Such closure arrangements are generally known in the art relating to other forms of surgical instruments, such as, for example, endocutters and the like. See, for example, U.S. Pat. No. 7,588,176 entitled SURGICAL CUTTING INSTRUMENT WITH IMPROVED CLOSURE SYSTEM and U.S. Pat. No. 7,665,647 entitled SURGICAL CUTTING AND STAPLING DEVICE WITH CLOSURE APPARATUS FOR LIMITING MAXIMUM TISSUE COMPRESSION FORCE, the disclosures of which are herein incorporated by reference in their respective entireties.

Figure 15:
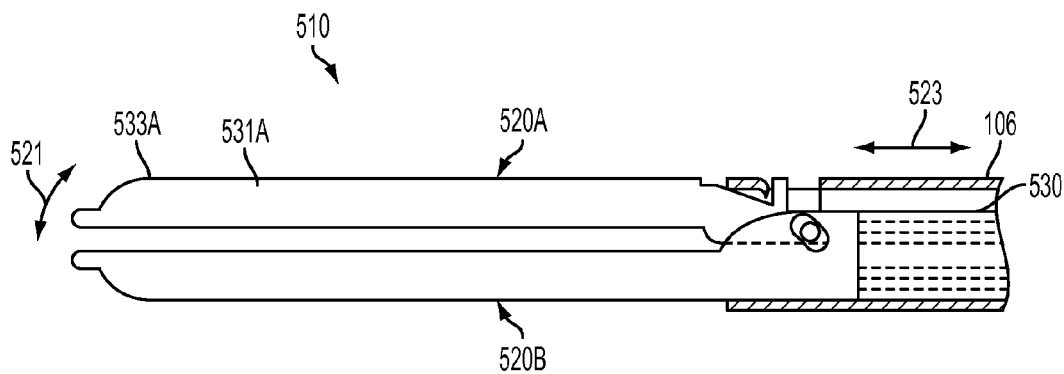
FIG. 15 is a side elevational view of an end effector according to another non-limiting embodiment of the present invention with the jaw members thereof in a closed position.
Figure 16:
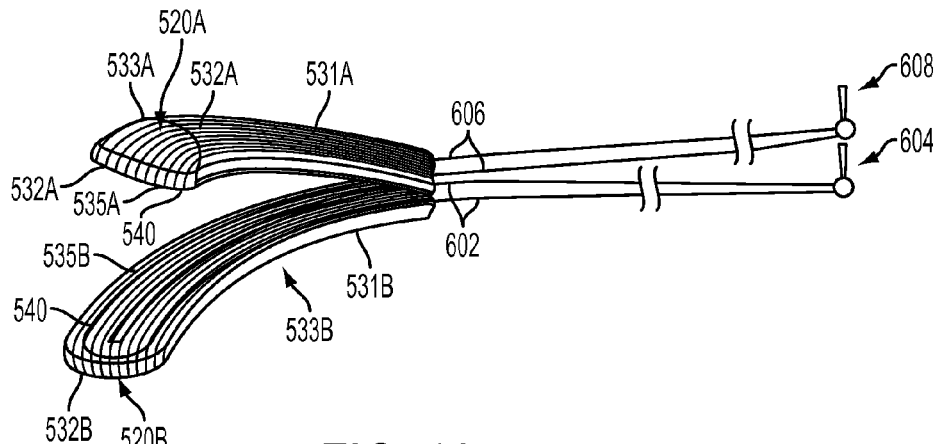
FIG. 16 is a partial perspective view of the end effector of FIG. 15 in an open position.

Referring now to FIG. 15, the first jaw 520A is pivotally coupled to the second jaw 520B for selective pivotal travel relative to the second jaw 520B (represented by arrow 521) upon the axial movement of the elongate tube 106 represented by arrow 523. First jaw 520A may comprise an upper first jaw body 531A that is formed from a series of vertically laminated layers 532A. See FIG. 16. In various embodiments, the laminated layers 532A may be fabricated from materials that comprise a thermal and/or electrical insulator, for example, zirconium, partially stabilized zirconium, aluminum oxide, silicon nitride, alumina-chromic, hydroxyapatite, other non-conductive glass materials, or other non-conductive ceramic materials. Other non-conductive glass-ceramic materials may be employed. The layers 532A may be laminated together by an elastomeric material such as, for example, polyisoprene, silicone, etc. The first jaw body 531A has an upper first outward-facing surface 533A and an upper first energy delivery surface 535A. Second jaw 520B may comprise a lower second jaw body 531B that is formed from another series of laminated layers 532B that may be fabricated and laminated from the various materials described above. The second jaw body 531B may have a lower second outward-facing surface 533B and a lower second energy delivery surface 535B. First energy delivery surface 535A and second energy delivery surface 535B may both extend in a "U" shape about the distal end of the end effector 510 and comprise vertical laminated layers of material. As discussed above, electrosurgical energy may be delivered through current paths between first energy delivery surface 535A and second energy delivery surface 535B. The first energy delivery surface 535A and the second energy delivery surface 535B may be configured to contact tissue and deliver electrosurgical energy to engaged tissue which is adapted to seal or weld the tissue. Opposing first and second energy delivery surfaces 535A and 535B may carry a variable resistive positive temperature coefficient (PTC) layer 540 that is coupled to electrical source 145 and controller 150 in series and parallel circuit components. First energy delivery surface 535A and the corresponding PTC layer 540 can have a negative polarity (−) while second energy delivery surface 535B and the corresponding PTC body 540 can have a positive polarity (+). PTC materials will "trip" and become substantially more resistive or non-conductive once a selected trip temperature is exceeded. First energy delivery surface 535A and second energy delivery surface 435B can carry any of the PTC matrix and electrode components in a laminated arrangement. Controller 150 can regulate the electrical energy delivered by electrical source 145 which in turn delivers electrosurgical energy to first energy delivery surface 535A and second energy delivery surface 535B. The energy delivery may be initiated by activation button 124 operably engaged with lever arm 128 and in electrical communication with controller 150 via cable 152. As mentioned above, the electrosurgical energy delivered by electrical source 145 may comprise radio frequency "RF" energy.

Figure 17:
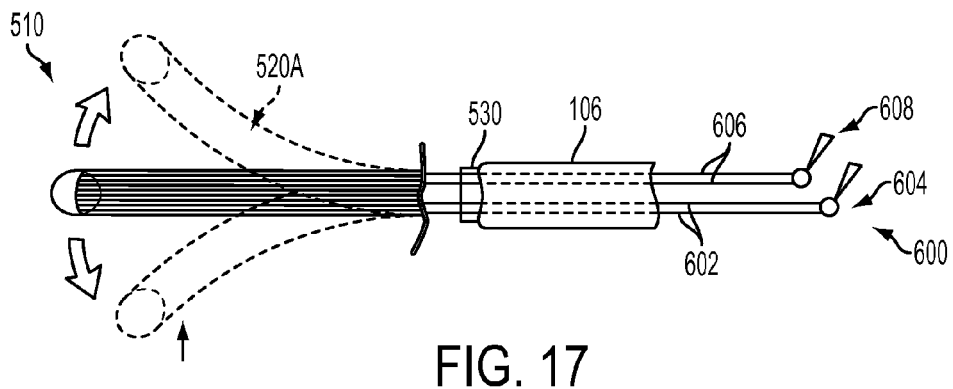
FIG. 17 is a top diagrammatical view of the end effector of FIGS. 15 and 16 with alternative flexed positions being shown in phantom.

To facilitate flexible travel of the end effector 510 in the manners, for example, depicted in FIG. 17, an actuating arrangement 600 of the type described above may be employed. In particular, the actuating arrangement may comprise left cables 602 and right cables 606 that are attached to the first jaw 520A and the second jaw 520B to essentially enable the clinician to "pull" the first jaw 520A and second jaw 520B to the left and right of the axis 125. The right cables 606 may extend through the hollow spine member 530 to be coupled to a right actuation member 608 that is operably supported by the handle 105'. See FIGS. 13 and 17. Similarly, the left cables 602 may extend through the hollow spine member 530 to be coupled to a left actuation member 604 that is operably supported by the handle 105'. For example, each actuation member 604, 608 may comprise a lever arm, button, etc. that is movably supported on the handle 105' and coupled to the corresponding cables 602, 606 such that movement of the actuation member 604, 608 in one direction applies tension to the cables 602, 606 and movement of the actuation member 604, 608 in another direction permits the cables 602, 606 to assume positions wherein the end effector 510 can assume a relatively coaxial orientation with the elongated member 106 to permit insertion of the end effector 510 through a lumen that will accept the hollow elongated member 106. The actuation members 604, 608 may be selectively lockable in the various positions using known locking arrangements. In still other embodiments, one or more motors may be employed to apply tension to and relieve tension from the cables to effectuate a desired flexing of the end effector 510.

Figure 18:
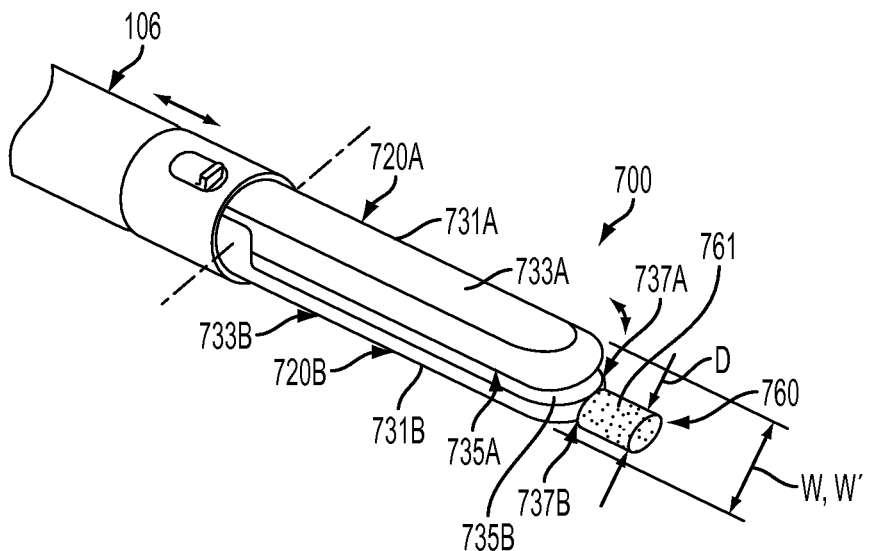
FIG. 18 is a perspective view of a portion of another end effector according to another non-limiting embodiment of the present invention.

FIG. 18 illustrates an end effector 700 according to another non-limiting embodiment of the present invention. End effector 700 may comprise a flexible end effector of the type described above or it could be essentially rigid. The end effector 700 has a first jaw 720A that is movably supported relative to a second jaw 720B. In various non-limiting embodiments, for example, the first jaw 720A may be pivotally coupled to or is otherwise pivotable relative to a second jaw 720B by means of the axial displacement of the elongate tube 106 in the various manners described above. As with various other embodiments described above, the first jaw 720A has a first jaw body 731A that has a width "W", an upper first outward-facing surface 733A, an upper first energy delivery surface 735A and a distal end 737A. Second jaw 720B may comprise a lower second jaw body 731B that also has a width "W'" which may or may not be identical to width "W" of the first jaw body 731A and thus enable the end effector 700 to be conveniently inserted through a trocar or other lumen. The second jaw body 731B may have a second outward-facing surface 733B, a second energy delivery surface 735B and a second distal end 737B. First energy delivery surface 735A and second energy delivery surface 735B may both extend in a "U" shape about the distal end of the end effector 700. The energy delivery surfaces 735A, 735B may otherwise operate in the various manners described above. In this embodiment, to assist the surgeon with dissecting the target tissue to be cauterized, a distally extending blunt tip 760 may be provided on one or both of the first and second jaws 735A, 735B. The blunt tip 760 may be relatively smooth or in other embodiments, the blunt tip 760 may be coated with or otherwise provided with fibrous structures 761 to allow better non-powered dissection. As can be seen in FIG. 18, the blunt tip 760 may have a diameter or width "D" that is less than the widths "W", "W'" to enable the tip 760 to be more easily inserted into areas in which the jaws 720A, 720B could not otherwise enter. In still other embodiments, an electrode (not shown) may be provided in the tip 760 such that it is configured to work as a monopolar dissector or alternatively a bipolar dissector.

Figure 19:
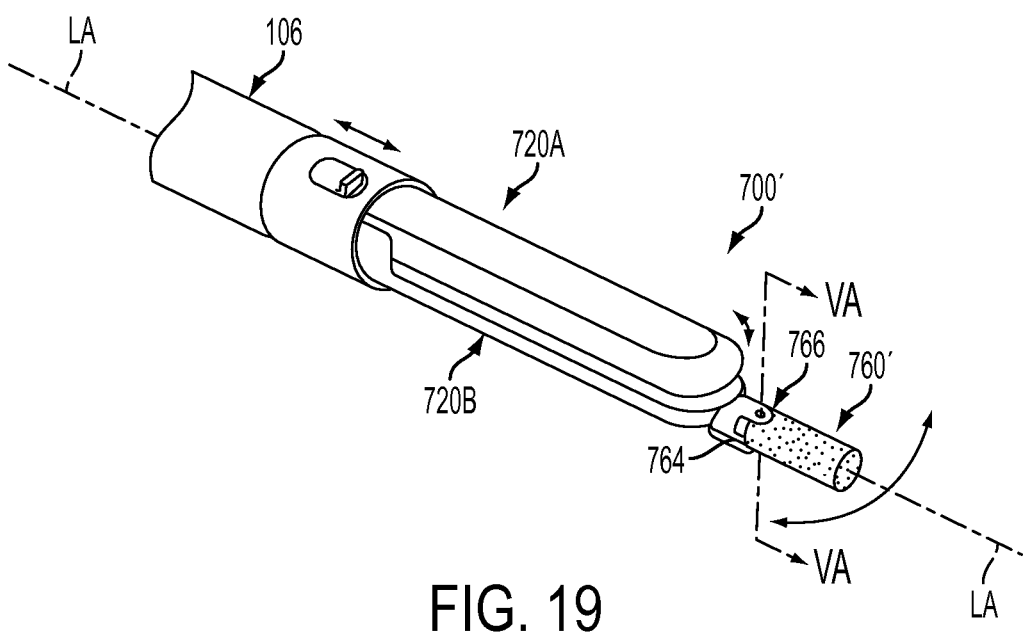
FIG. 19 is a perspective view of a portion of another end effector according to another non-limiting embodiment of the present invention.

In other non-limiting embodiments, the end effector 700' may have a blunt tip portion 760' that is pivotally coupled to an extension 764 that protrudes from one or both of the first and second jaws 720A, 720B. See FIG. 19. The blunt tip portion 760' may be pivotally coupled to the extension 764 by a hinge 766 that will frictionally retain the blunt tip portion 760' in a desired articulated position. For example, the surgeon may bring the blunt tip portion 760' into contact with tissue or other structure to pivot the blunt tip portion 760' to a desired position about a vertical axis VA-VA that is substantially transverse to a longitudinal axis LA-LA. The blunt tip portion 760' may be retained in that position by friction between the components of the hinge 766. While FIG. 19 illustrates that the blunt tip portion is attached to the extension 764 for pivotal travel about a vertical axis, the blunt tip portion 760' may be attached to the extension 764 for selective pivotal travel about a horizontal axis (not shown). In still other non-limiting embodiments, the blunt tip portion 760' may be movably coupled to the extension by a "universal" hinge arrangement that facilitates pivotal positioning of the blunt tip portion 760' about a horizontal axis and a vertical axis and thereafter retained in such desired position by friction. In still other non-limiting embodiments, the blunt tip portion 760 may be attached to extension 764 by a plurality of hinges and intermediate tip portions to further enable the blunt tip portion to be positioned in a desired orientation for dissection purposes. Alternatively, the blunt tip portion may be formed on the jaw members(s) and be constructed of a malleable material that allows the user to pre-sect the shape prior to insertion into the patient or after insertion with the use of another instrument.

Figure 20:
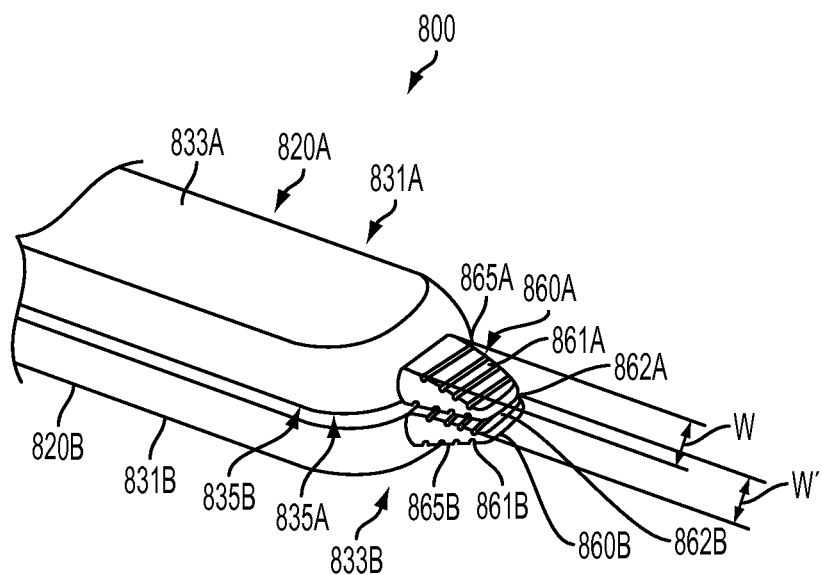
FIG. 20 is a perspective view of a portion of another end effector according to another non-limiting embodiment of the present invention.
Figure 21:
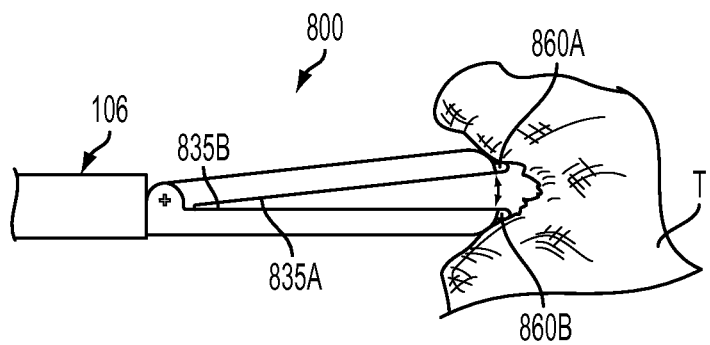
FIG. 21 is a side view of the end effector embodiment of FIG. 20 being used to dissect tissue.
Figure 22:
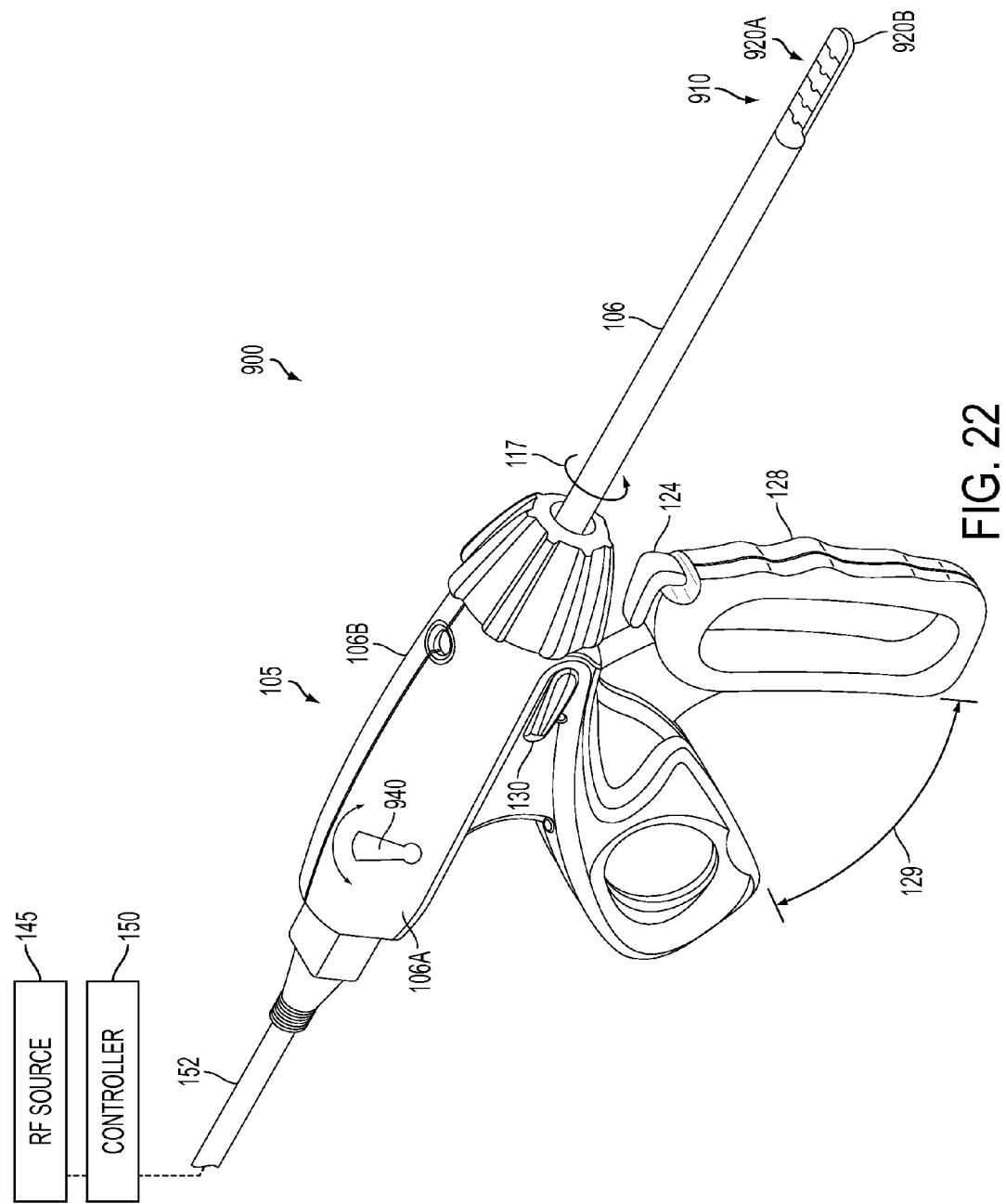
FIG. 22 is a perspective view of an electrosurgical instrument according to another non-limiting embodiment of the present invention.

FIGS. 20 and 21 illustrate an end effector 800 of another non-limiting embodiment of the present invention that may be identical to the end effector 700 except for the differences noted below. End effector 800 may comprise a flexible end effector of the type described above or it could be essentially rigid (not capable of flexing out of axial alignment with the elongate tube 106). The end effector 800 has a first jaw 820A that is pivotally coupled to or is otherwise pivotable relative to a second jaw 820B by means of the axial displacement of the elongate tube 106 in the various manners described above. As with various other non-limiting embodiments described above, the first jaw 820A has a first jaw body 831A that has a first outward-facing surface 833A and a first energy delivery surface 835A. Second jaw 820B may comprise a lower second jaw body 831B that has a second outward-facing surface 833B and a second energy delivery surface 835B. First energy delivery surface 835A and second energy delivery surface 835B may both extend in a "U" shape about the distal end of the end effector 800. The energy delivery surfaces 835A, 835B may otherwise operate in the various manners described above. In this embodiment, to assist the surgeon with dissecting or otherwise separating the target tissue to be cauterized, a distally extending first tip 860A may be provided on the first jaw 820A and a distally extending second tip 860B may be provided on the second jaw 820B. The first tip 860A may have a tapered outwardly facing surface 861A and a relatively planar inwardly facing surface 862A. Tissue gripping grooves 865A or bumps or other structures may be provided on the outer facing surface 861A and or inwardly facing surface 862A. Similarly, the second tip 860B may have a tapered outwardly facing surface 861B and a relatively planar inwardly facing surface 862B. Tissue gripping grooves 865B or bumps or other structures may be provided on the outer facing surface 861B and/or the inwardly facing surface 862B.

In various non-limiting embodiments, the first and second tips 860A, 860B are not powered. In other non-limiting embodiments, however, the tip 860A comprises a portion of the first energy delivery surface 835A or otherwise has an electrode portion therein. Likewise, the second tip 860B comprises a portion of the second energy delivery surface 835B or otherwise has an electrode portion therein. When powered, the energy may arc from tip to tip in a bipolar configuration or tip to tissue in a monopolar configuration. FIG. 21 illustrates one potential use of the end effector 800 to separate or dissect tissue "T".

FIGS. 22-25 illustrate an electrosurgical instrument 900 according to another non-limiting embodiment of the present invention. This non-limiting embodiment may employ a handle 105' that is somewhat similar to handle 105 described above. However, the electrosurgical instrument 900 does not employ a translatable member that is designed to cut tissue and close the jaws 920A and 920B of an end effector 910. In this embodiment, the second jaw 920B is coupled to a spine member 930 (FIG. 23) that extends through the hollow elongate tube 106 and is attached to the handle 105' in the manner described above. Axial travel of the elongate tube 106 causes the first jaw 920A to pivot relative to the second jaw 920B. Other jaw closing mechanisms may also be employed.

Figure 23:
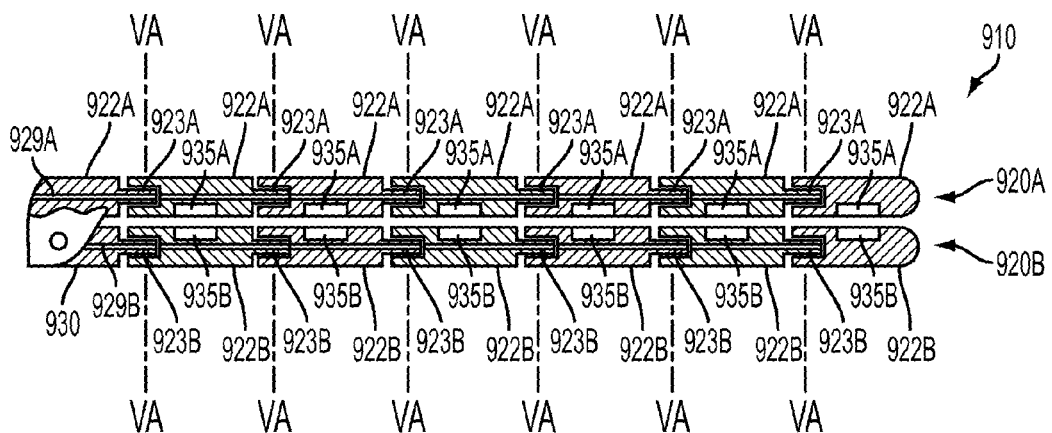
FIG. 23 is a cross-sectional view of the end effector depicted in FIG. 22 in a closed position.
Figures 24, 25:
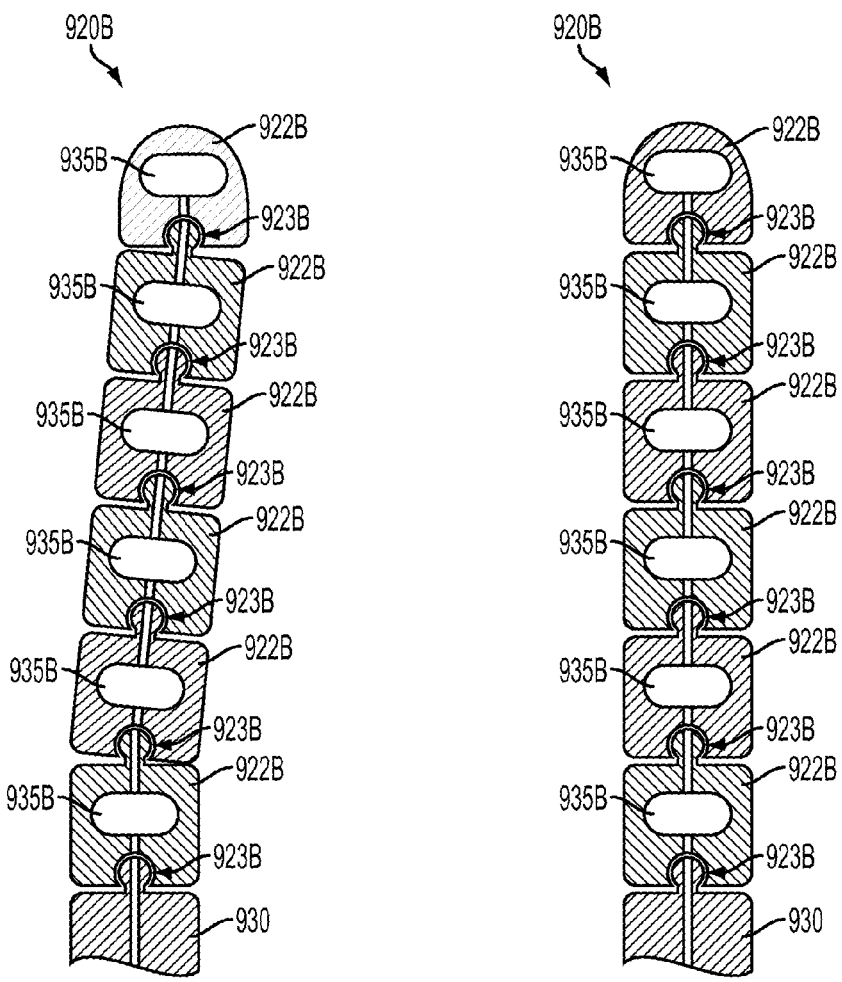
FIG. 24 is a top cross-sectional view of the lower jaw of the end effector of FIG. 23 in a partially articulated position.
FIG. 25 is another top cross-sectional view of the lower jaw of FIG. 24 in a straight position.

First jaw 920A may comprise a series of pivotally interconnected first body segments 922A as shown in FIGS. 23-25. The first body segments 922A are coupled together by a ball and socket-type joint arrangement 923A such that they may pivot relative to each other about a vertical axis VA-VA as shown in FIG. 23. Each first body segment 922A may be fabricated from, for example, a thermal and/or electrical insulator. For example, zirconium, partially stabilized zirconium, aluminum oxide, silicon nitride, alumina-chromic, hydroxyapatite, other non-conductive glass materials, other non-conductive ceramic materials, and other non-conductive glass-ceramic materials may be employed. Each first body segment 922B further has a first energy delivery electrode 935A mounted therein.

Similarly, the second jaw 920B may comprise a series of pivotally interconnected second body segments 922B that are pivotally interconnected by a ball and socket-type joint arrangement 923B as shown in FIGS. 24 and 25. The second body segments 922B are coupled together such that they may pivot relative to each other about the vertical axes VA-VA as shown in FIG. 23. Each second body segment 922B corresponds to a first body segment 922A and may be fabricated from, for example, the same or different material comprising the corresponding first body segment 922A. Each second body segment 922B further has a second energy delivery electrode 935B mounted therein that corresponds to, and is substantially vertically aligned with, the first energy delivery electrode 935A in the corresponding first body segment 922A. The first energy delivery electrodes 935A and the second energy delivery electrodes 935B may be configured to contact tissue and deliver electrosurgical energy to engaged tissue which is adapted to seal or weld the tissue. Opposing first and second energy delivery electrodes 935A and 935B may be coupled to electrical source 145 and controller 150 in series and parallel circuit components. First energy delivery electrode 935A and the first body segment 922A can have a negative polarity (−) while second energy delivery surface 935B and the corresponding second body segment 922B can have a positive polarity (+) or vice versa. The first and second body segments 922A, 922B materials may "trip" and become resistive or non-conductive once a selected trip temperature is exceeded. Controller 150 can regulate the electrical energy delivered by electrical source 145 which in turn delivers electrosurgical energy to the first energy delivery electrodes 935A and the second energy delivery electrodes 9353B. The energy delivery may be initiated by activation button 124 operably engaged with lever arm 128 and in electrical communication with controller 150 via cable 152. As mentioned above, the electrosurgical energy delivered by electrical source 145 may comprise radio frequency "RF" energy and may be either monopolar or bipolar in nature.

In various non-limiting embodiments, once the first body segments 922A are oriented in a desired orientation relative to each other, friction between the ball and socket components 923A serve to retain the first body segments 922A in that position. Similarly, once the second body segments 922B are oriented in a desired orientation relative to each other, friction between the ball and socket components 923B retain the second body segments 922B in that position. Optionally, a first locking cable 929A may extend from a locking mechanism on the handle 105' through each first body segment 922A to the distal-most body segment 922A. Once the body segments 922A have been moved to a desired orientation, the surgeon may apply tension to the first locking cable 929A by means of the locking mechanism to pull the first body segments 922A together to thereby lock them in place. Likewise, a second locking cable 929B may extend from the locking mechanism 940 or another locking mechanism on the handle 105' through each body segment 922B to the distal-most body segment 922B. Once the body segments 922B have been moved to the desired orientation, the surgeon may apply tension to the second locking cable 929B to pull the second body segments 922B together to thereby lock them in place.

Figure 26:
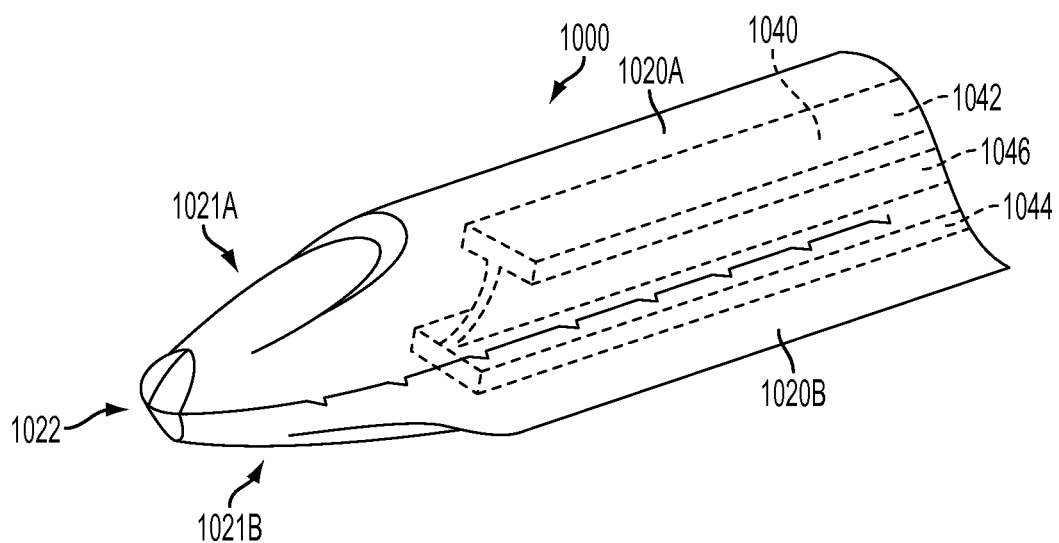
FIG. 26 is a partial perspective view of an end effector according to another non-limiting embodiment of the present invention with a portion of a translatable member thereof shown in phantom.
Figure 27:
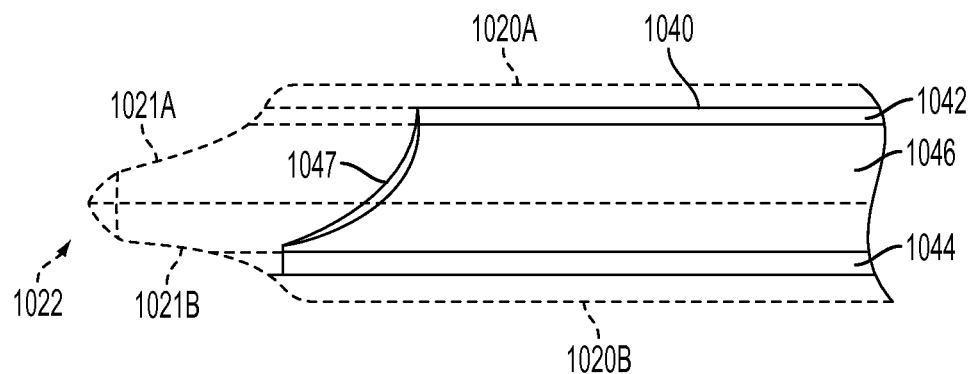
FIG. 27 is a side elevational view of a portion of the translatable member depicted in FIG. 26 with the end effector jaw portions shown in phantom.
Figure 28:
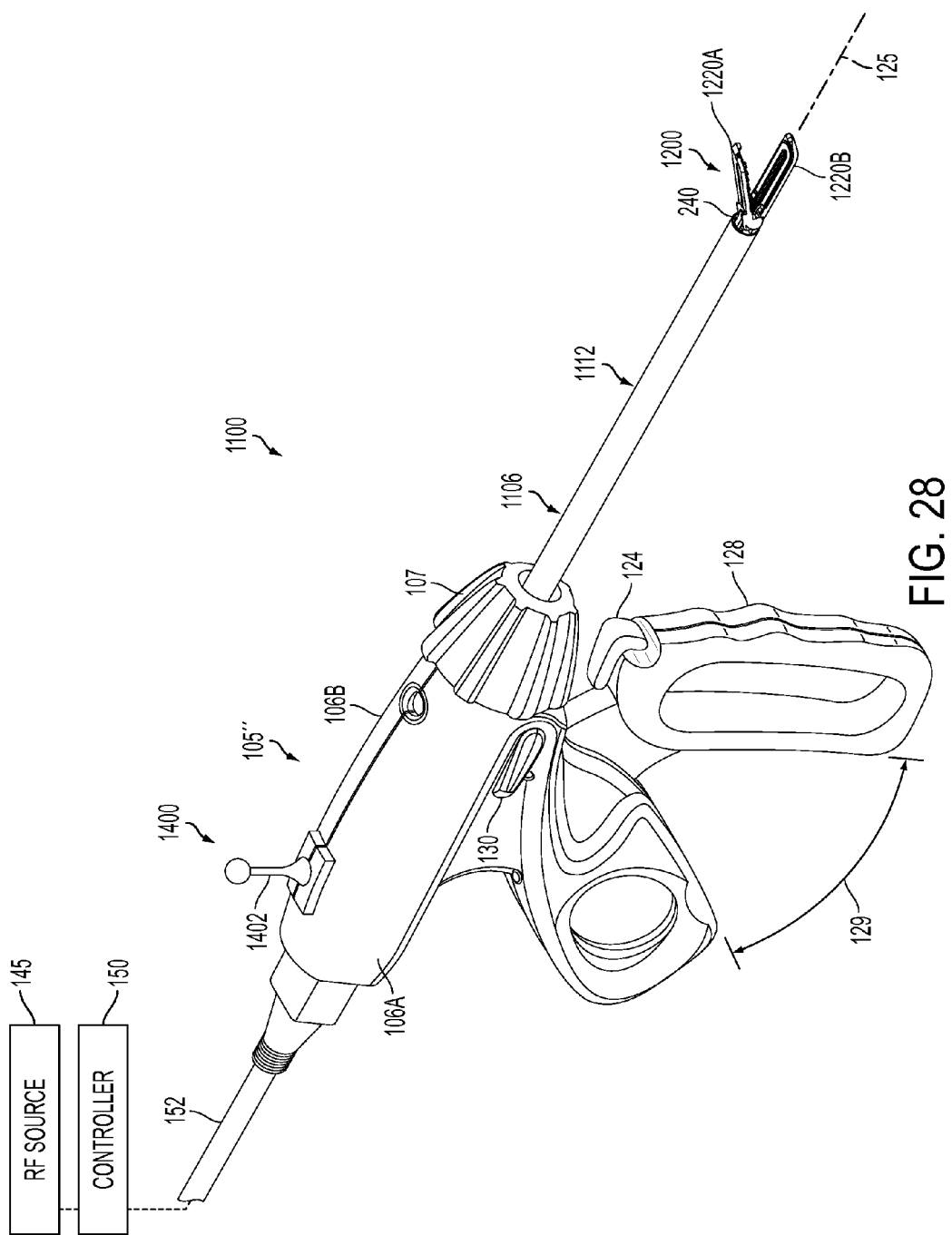
FIG. 28 is a perspective view of an electrosurgical instrument according to another non-limiting embodiment of the present invention.

FIGS. 26 and 27 illustrate a portion of an end effector 1000 of another non-limiting embodiment of the present invention that includes a first jaw 1020A and a second jaw 1020B. The first jaw 1020A may have a first tapered distal end portion 1021A and the second jaw 1020B may have a second tapered distal end portion 1021B that converges with the first tapered distal end portion 1021A to form a substantially conical end effector tip 1022 that is particularly well-suited for dissection purposes. The embodiment may further include a reciprocating I-beam member 1040 that may be identical in construction and operation as the I-beam members described above, except for the following differences. More specifically, as can be seen in FIG. 27, the I-beam member 1040 has an upper flange 1042 and a lower flange 1044 that are interconnected by a central web portion 1046. The central web portion 1046 extends through aligned slots (not shown) in the first jaw member 1020A and the second jaw member 1020B in the manner described above. The upper flange 1042 may ride in a groove, slot or recessed area in the first jaw member 1020A and the lower flange 1044 may ride in a groove, slot or recessed area in the second jaw member 1020B such that, as the I beam member 1040 is distally advanced through the first and second jaw members 1020A, 1020B, the upper and lower flanges 1042, 1044 pivot the first and second jaws 1020A, 1020B together in the manner described above. As can be most particularly seen in FIG. 27, the lower flange 1044 protrudes further in the distal direction than does the upper flange 1042. The portion of the central web 1046 that extends from the distal-most edge of the lower flange 1044 to the distal-most edge of the upper flange 1042 has a cutting edge 1047 formed thereon. In various embodiments, the cutting edge 1047 may have an arcuate profile when viewed from the side. See, for example, FIG. 27. Such "recessed" I-beam arrangement, with an arcuate cutting surface, in combination with the tapered distal tip of the end effector, allows some compression of the first and second jaws 1020A, 1020B without transecting the tissue clamped between the first and second jaws 1020A, 1020B. Stated another way, as the I-beam is advanced distally within the end effector, the portion of the cutting surface that protrudes out of the slot in the second jaw 1020B is proximal to the distal most end of the portion of I-beam advancing through the second jaw 1020B. In various applications, the jaws can be actuated to add surface coagulation to cutting for tissue laying on the extended portion of the lower jaw, for example. In still other non-limiting embodiments, the distal edge of the web (i.e., edge 1047) may have a "C" shape or "U" shape. Stated another way, when viewed from the side, the edge 1047 may form a substantially horizontal "U" shape. Such unique I-beam configurations facilitate the compression of tissue between the jaws which serves to drive out water from the tissue. Current is then applied to the compressed tissue before it is ultimately cut with the advancing cutting edge. As a result, more robust seals are generally attained.

FIGS. 28-31 illustrate an electrosurgical instrument 1100 according to another non-limiting embodiment of the invention. Electrosurgical instrument 1100 comprises a proximal handle end 105", a distal end effector 1200 and an introducer or elongate shaft member 1106 disposed in-between. In this non-limiting embodiment, however, the elongate shaft member 1106 includes a flexible spine assembly 1110 that is enclosed in a flexible hollow sheath 1112.

Figure 29:
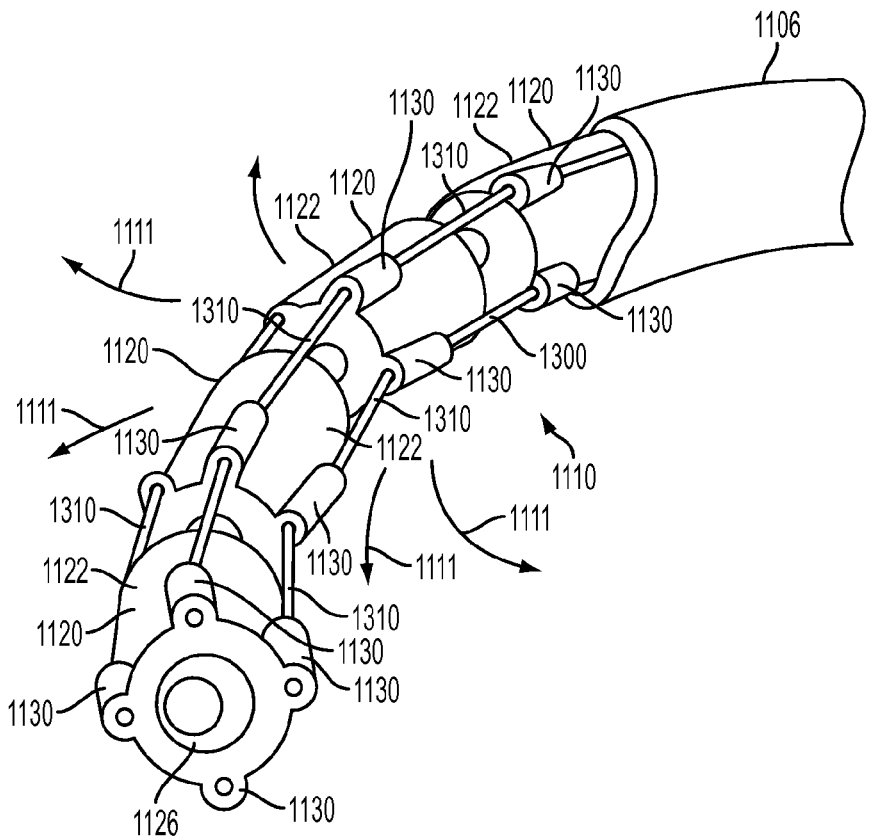
FIG. 29 is a partial perspective view of a portion of an articulatable elongate shaft according to a non-limiting embodiment of the present invention.
Figure 30:
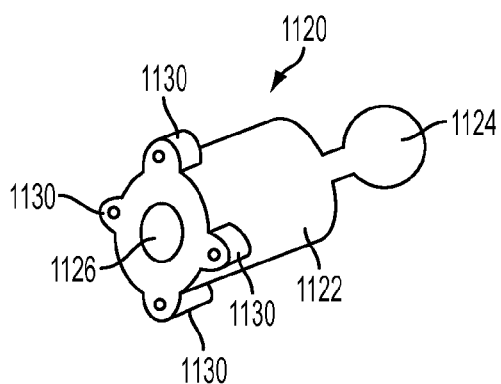
FIG. 30 is a perspective view of a spine segment according to an embodiment of the present invention.
Figure 31:
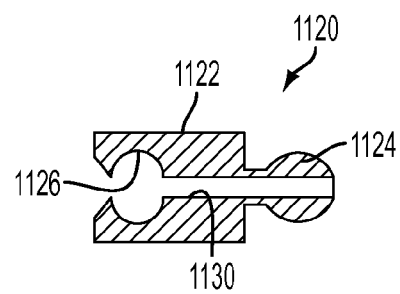
FIG. 31 is a cross-sectional view of the spine segment of FIG. 30.
Figure 32:
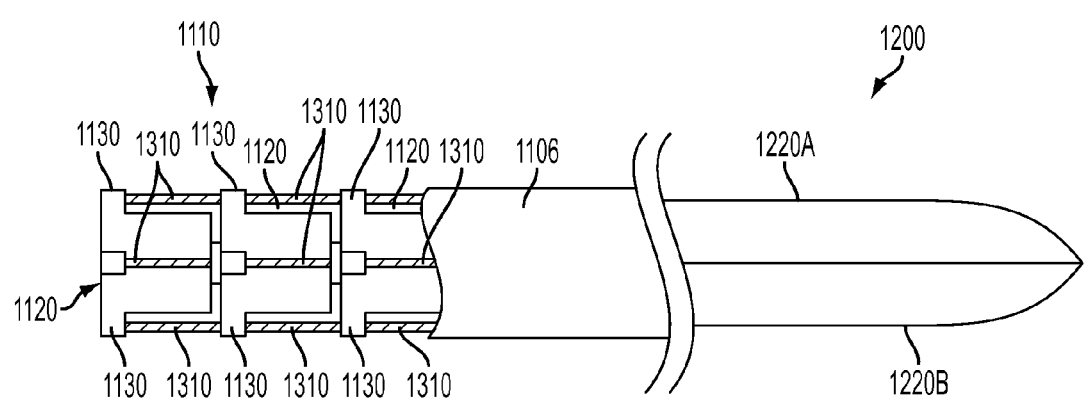
FIG. 32 is a partial side elevational view of the articulatable elongate shaft depicted in FIGS. 29-31 attached to an end effector.

FIGS. 29-31 illustrate various spine assembly components. In particular, in at least one non-limiting embodiment, the spine assembly 1110 may be fabricated from a plurality of interconnected spine segments 1120. As can be seen in FIGS. 30 and 31, each spine segment 1120 has a hollow body 1122 that is somewhat cylindrical in shape. One end of the hollow body 1122 has an outwardly protruding ball member 1124 formed thereon. The other end of the body 1122 has a socket 1126 that is sized to rotatably receive and retain the ball member 1124 of an adjacent segment 1120 therein. In various embodiments, the proximal-most segment 1122 may be non-movably attached to actuator wheel 107 rotatably supported on the handle 105". See FIG. 28. Thus, rotation of the actuator wheel 107 will cause the spine assembly 1110 to rotate about axis 125. The distal-most spine segment 1120 is attached to the end effector 1200. In one embodiment, the end effector 1200 may include a set of operable-closeable jaws 1220A and 1220B. The end effector 1200 may be adapted for capturing, welding and transecting tissue. First jaw 1220A and second jaw 1220B may close to thereby capture or engage tissue therebetween. First jaw 1220A and second jaw 1220B may also apply compression to the tissue. The second jaw 1220B may be attached to the distal-most spine segment 1120 and the first jaw 1220A may be pivotally or otherwise movably coupled to the second jaw 1220B. In one embodiment, for example, the end effector 1200 may be identical in construction and operation to end effector 200 described in detail above.

The electrosurgical instrument 1110 may also employ a translatable, reciprocating member or reciprocating "I-beam" member 240. The lever arm 128 of handle 105'' may be adapted to actuate a flexible translatable member 240 which also functions as a jaw-closing mechanism. For example, translatable member 240 may be urged distally as lever arm 128 is pulled proximally along path 129. The distal end of translatable member 240 comprises a flexible flanged "I"-beam that is configured to interface with the first and second jaw members 1220A, 1220B in the manner described above. The flexible translatable member 240 extends through the lumen 1130 provided through each spine segment 1120. See FIG. 31. The distal end of the flexible translatable member 240 interfaces with the first and second jaws 1220A, 1220B in the manner described above. Wires for powering the end effector 1200 may also extend through the lumen 1130 or extend through other passages (not shown) in the spine segments 1120. The unique and novel aspects of the spine assembly 1110 may also be employed with a host of other end effector arrangements. For example, the lumens 1130 in the spine segments 1120 may accommodate a variety of different actuator arrangements, wires, cables etc. that may be used to control and actuate the end effector.

The spine assembly 1110 may be effectively flexed in more than two directions (some of which are represented by arrows 1111 in FIG. 29) by a control assembly generally designated as 1300. In various embodiments, for example, control assembly 1300 may comprise at least one actuation member 1310 that extends through corresponding aligned hollow lugs 1130 formed on the perimeter of the hollow body 1122 of each spine segment 1120. In the depicted embodiment, the actuation members 1310 comprise four control cables. In alternative embodiments, however, three control cables could be employed to essentially achieve the same degrees of motion achieved with four cables. U.S. Pat. No. 8,262,563, entitled ENDOSCOPIC TRANSLUMENAL ARTICULATABLE STEERABLE OVERTUBE, the disclosure of which is herein incorporated by reference, discloses other steerable tubular arrangements that may be employed. In alternative embodiments, the control members 1310 may also comprise electrical conductors that communicate with the RF source to carry the RF energy to the end effector.

In the illustrated non-limiting embodiment, each spine segment 1122 has four diametrically opposed lugs 1130 formed thereon. Each of the control cables 1310 extend through the hollow sheath 1106 and into the handle 105'' to interface with articulation control mechanism 1400. In the depicted embodiment, the articulation control mechanism 1400 comprises a joy stick arrangement 1402 that is operably supported by the handle 105''. Thus, movement of the joy stick arrangement 1402 will apply tension to one or more of the cables 1310 to thereby cause the spine assembly 1110 to articulate. Other cable control arrangements could also be employed.

Figure 33:
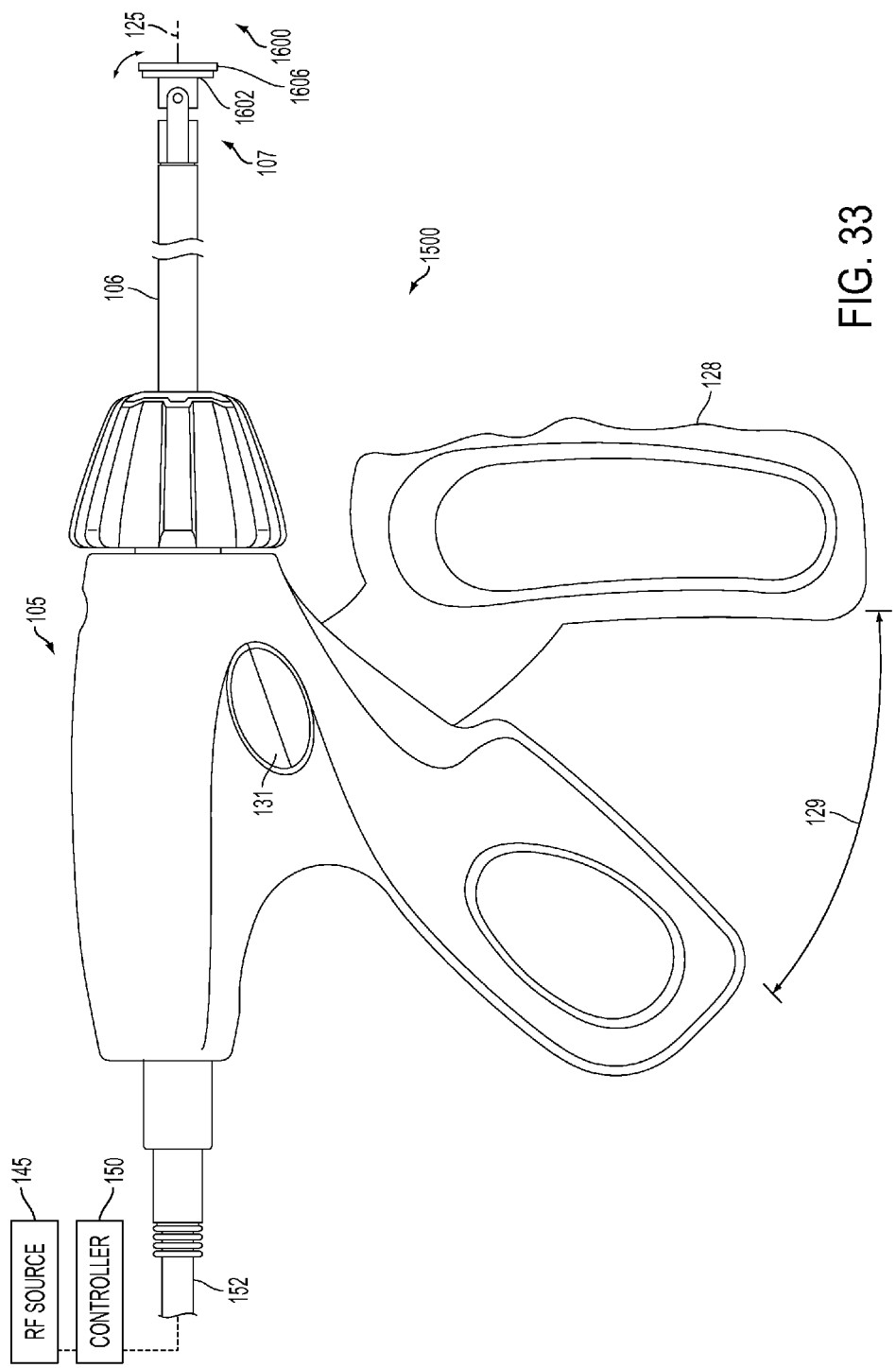
FIG. 33 is a side elevational view of an electrosurgical instrument according to another non-limiting embodiment of the present invention.
Figure 34:
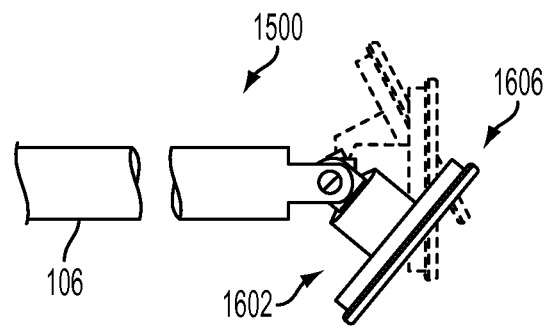
FIG. 34 is a side elevational view of the end effector depicted in FIG. 33, with alternative positions illustrated in phantom.
Figure 35:
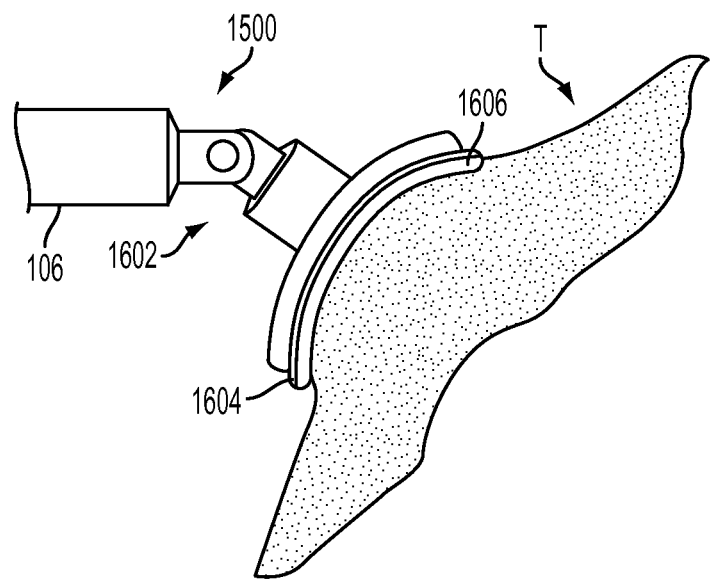
FIG. 35 is another side elevational view of the end effector of FIG. 34 engaging tissue.

FIGS. 33-35 illustrate a monopolar electrosurgical instrument 1500 according to another non-limiting embodiment of the present invention. Electrosurgical instrument 1500 comprises a proximal handle 105, a distal end effector 1600, and an introducer or elongated shaft member 106 disposed in-between. The end effector 1600 in conjunction with a return pad (not shown) may be adapted for controlled surface ablation in Barrett's esophagus, liver or endometriosis procedures. As will be discussed in further detail below, the end effector 1600 is movable relative to the elongate shaft 106 which makes it particularly well-suited for laparoscopic or open procedural use.

Handle 105 may comprise a lever arm 128 which may be pulled along a path 129. The handle 105 can be any type of pistol-grip or other type of handle known in the art that is configured to carry actuator levers, triggers, etc. Elongate shaft 106 may have a cylindrical or rectangular cross-section and can comprise a thin-wall tubular sleeve that extends from handle 105. Elongate shaft 106 may be fabricated from, for example, metal such as stainless steel or plastics such as Ultem®, or Vectra®, etc. In still other embodiments, the elongate shaft 106 may comprise a polyolefin heat shrunk tube and have a bore extending therethrough for carrying actuator cables or members as well as for carrying electrical leads for delivery of electrical energy to electrosurgical components of end effector 1600. The elongate shaft member 106 along with the end effector 1600 may, in some embodiments, be rotatable a full 360° about an axis 125, relative to handle 105 through, for example, a rotary triple contact.

The end effector 1600 may comprise a pad support 1602 that is pinned or otherwise movably coupled to a distal end 107 of the elongate shaft 106. In various embodiments, the pad support 1602 may be fabricated from relatively flexible material such as, for example, poly carbonate or a relatively high durometer silicone elastomer. However, other materials may be employed. Attached to the flexible pad support 1602 is a conductor or electrode element 1604 and a flexible pad member 1606 that is fabricated from positive temperature coefficient (PTC) material. For example, the flexible pad member 1604 may be fabricated from that PTC material disclosed in U.S. Pat. No. 6,770,072, entitled ELECTROSURGICAL JAW STRUCTURE FOR CONTROLLED ENERGY DELIVERY, the disclosure of which is herein incorporated by reference in its entirety. The conductor or electrode element 1604 may be fabricated from, for example, metals such as stainless steel or copper and be coupled to an RF source 145 and controller 150 through electrical leads in cable 152. Such end effector 1600 includes an activation control button 131 that facilitates the application of controlled energy to tissue. The energy delivery may be initiated by activation button 131 in electrical communication with controller 150 via cable 152. As mentioned above, the electrosurgical energy delivered by electrical source 145 may comprise radio frequency "RF". Lever 128 can provide control of the pad support 1602 relative to the elongate shaft 106 for better alignment and approximation of the pad 1602 to the tissue. The lever 128 may alternatively control articulation of the elongate shaft proximal the distal end of the elongate shaft 107.

This embodiment of the present invention provides the ability to supply current/power to targeted tissue at a predetermined critical temperature level. This is accomplished when the applied RF energy to the tissue reaches the point in time that the PTC pad 1606 is heated to its selected switching range. Thereafter, current flow from the conductive electrode 1604 through the flexible pad 1606 will be terminated due to the exponential increase in the resistance of the PTC to provide instant and automatic reduction of RF energy. Thus, the end effector 1600 can automatically modulate the application of energy to tissue between active RF heating and passive conductive heating to maintain a target temperature level. In various embodiments, the PTC pad 1606 is engineered to exhibit a dramatically increasing resistance above a specific temperature of the material. The energy delivery electrode 1604 is applied internally to the patient's body. A grounding pad applied externally to the patient's body completes the circuit. The PTC material 1606 will "trip" and become resistive or non-conductive once a selected trip temperature is exceeded. As can be seen in FIG. 35, the flexible nature of the end effector components enables the end effector to somewhat conform to irregular tissue "T". These various embodiments may be employed to treat tissues, such as, for example, liver tissue, lung tissue cardiac tissue, prostate tissue breast tissue vascular tissue, etc. by the application of radio frequencies thereto. The device can be constructed for laparoscopic or open procedures. The flexible end effector can be designed to allow access through an access port such as a trocar. Further, the end effector can effectively apply controlled energy to the tissue. The term "controlled" refers to the ability to provide current/power to targeted tissue at a predetermined critical temperature level. This may be accomplished when the RF energy is applied to the tissue reaches the point in time that the PTC material is heated to is selected switching range. Thereafter, current flow from the conductive electrode through the flexible engagement surface may be terminated due to the exponential increase in the resistance of the PTC to provide instant and automatic reduction of RF energy. Thus, the flexible end effector can automatically modulate the application of energy to tissue between active RF heating and passive conduct heating to maintain a target temperature level.

Figure 36:
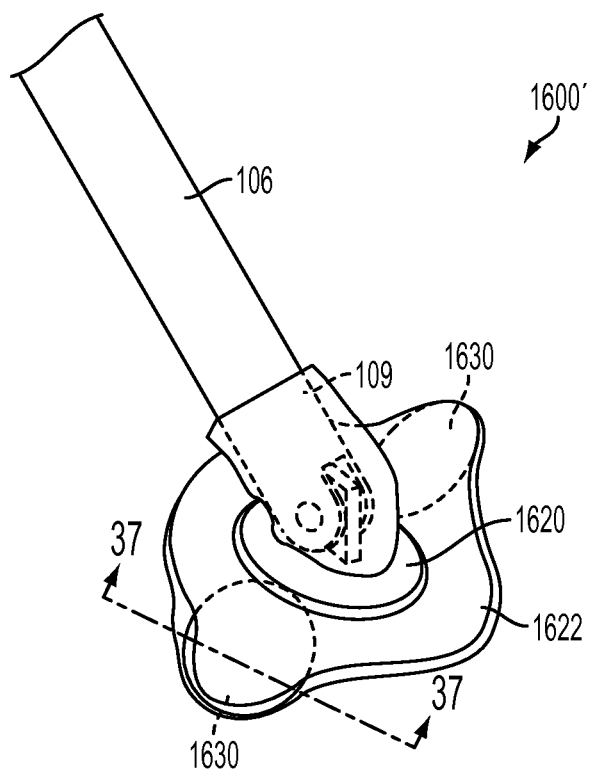
FIG. 36 is a perspective view of an end effector according to another embodiment of the present invention.
Figure 37:
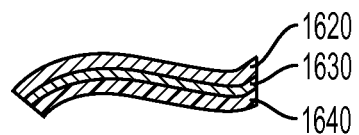
FIG. 37 is a cross-sectional view of a portion of the end effector of FIG. 36 taken along line 37-37 in FIG. 36.

FIGS. 36 and 37 depict another end effector 1600' that is similar to end effector 1600 described above except for the differences noted below. As can be seen in FIG. 36, the elongate shaft 106 is attached to a yoke 109. The elongate shaft 106 may be fabricated from an insulator material such as Ultem®, Vectra, etc. or a conductive material such as stainless steel. In other embodiments, for example, the elongate shaft 106 may be fabricated from a polyolefin heat shrunk tube. Yoke 109 may be fabricated from an elastomer such as, for example, polyurethane or a shrink material such as a polyolefin, polyvinylchloride (PVC) or Neoprene. Yoke 109 is pivotally attached to a rigid pad portion 1620 that may be fabricated from, for example, polycarbonate or a high durometer silicone elastomer. The rigid pad portion 1620 is attached to a flexible pad portion 1622 by, for example, an elastomeric adhesive or overmolding process. Flexible pad portion 1622 may be fabricated from polyisoprene or silicone. The flexible pad portion 1622 may also be fabricated from closed or open cell Neoprene or silicone foam. In the embodiment depicted in FIG. 36, two (conductive) made from stainless steel, copper, etc.) electrodes 1630 are attached to the flexible pad portion 1622 by, for example, an elastomeric adhesive and are attached to the controller and source of RF energy by cables that extend through the elongate shaft 106 and handle. In one non-limiting embodiment, the two electrodes 1630 may serve as the source and return of the electrical circuit, as in a bipolar instrument. In another non-limiting embodiment, the two electrodes may be electrically connected and serve as a single source with an external patient return as in a monopolar instrument. In other embodiments, a single conductive electrode which may be substantially coextensive with the flexible pad portion may be employed. A flexible PTC member 1640 may be attached to the electrode(s) 1630 by, for example, adhesive or mechanically attached. This embodiment may be operated in the manner described above.

The devices disclosed herein may be designed to be disposed of after a single use, or they may be designed to be used multiple times. In either case, however, the device may be reconditioned for reuse after at least one use. Reconditioning may include a combination of the steps of disassembly of the device, followed by cleaning or replacement of particular pieces, and subsequent reassembly. In particular, the device may be disassembled, and any number of particular pieces or parts of the device may be selectively replaced or removed in any combination. Upon cleaning and/or replacement of particular parts, the device may be reassembled for subsequent use either at a reconditioning facility, or by a surgical team immediately prior to a surgical procedure. Those of ordinary skill in the art will appreciate that the reconditioning of a device may utilize a variety of different techniques for disassembly, cleaning/replacement, and reassembly. Use of such techniques, and the resulting reconditioned device, are all within the scope of this application.

Preferably, the various embodiments of the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. Other sterilization techniques can be done by any number of ways known to those skilled in the art including beta or gamma radiation, ethylene oxide, and/or steam.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:
1. A surgical instrument, comprising:
   an elongate shaft;
   an end effector extending from said elongate shaft, said end effector comprising:
      a first member; and
      a second member, wherein said first member is movable relative to said second member to transition said end effector between an open configuration and an approximated configuration to clamp tissue between said first member and said second member; and a camming assembly movable along a curved path, said camming assembly comprising:
- a first camming member, wherein said first camming member comprises:
  - a first distal camming portion;
  - a first proximal camming portion; and
  - a first flexible portion extending between said first distal camming portion and said first proximal camming portion;
- a second camming member, wherein said second camming member comprises:
  - a second distal camming portion;
  - a second proximal camming portion; and
  - a second flexible portion extending between said second distal camming portion and said second proximal camming portion; and
- a connector at least partially disposed between said first camming member and said second camming member, wherein said connector comprises a cutting member at a distal portion thereof, and wherein said camming assembly is movable relative to said end effector to exert a camming force against said first member and said second member to transition said end effector to said approximated configuration.

2. The surgical instrument of claim 1, wherein at least one of said first flexible portion and said second flexible portion is fabricated from an elastic alloy.

3. The surgical instrument of claim 1, wherein said elongate shaft comprises a flexible portion.

4. The surgical instrument of claim 1, wherein at least one of said first member and said second member comprises an electrode.

5. The surgical instrument of claim 1, wherein at least one of said first camming member and said second camming member defines a plane intersected by said cutting member.

6. The surgical instrument of claim 1, wherein said first member comprises a first channel configured to receive at least a portion of said first camming member.

7. The surgical instrument of claim 6, wherein said second member comprises a second channel configured to receive at least a portion of said second camming member.

8. The surgical instrument of claim 1, wherein at least one of said first flexible portion and said second flexible portion comprises a plurality of cutout portions.

9. The surgical instrument of claim 8, wherein each said cutout portion comprises a first region and a second region, wherein said first region is narrower than said second region, and wherein said second region is further away from said connector than said first region.

10. The surgical instrument of claim 1, wherein said first flexible portion comprises a first plurality of cutout portions, wherein said second flexible portion comprises a second plurality of cutout portions, and wherein at least one of said first plurality of cutout portions is aligned with at least one of said second plurality of cutout portions.

11. The surgical instrument of claim 1, wherein said camming assembly is formed in the shape of an I-beam.

12. A surgical instrument, comprising:
an elongate shaft;
an end effector extending from said elongate shaft, said end effector comprising:
- a first jaw; and
- a second jaw, wherein said first jaw is movable relative to said second jaw to transition said end effector between an open configuration and an approximated configuration to clamp tissue between said first jaw and said second jaw; and
- a bendable firing member movable along a non-linear path, said bendable firing member comprising:
  - a first bendable portion defining a first plane, said first bendable portion comprising a first camming surface at a distal portion thereof;
  - a second bendable portion defining a second plane, said second bendable portion comprising a second camming surface at a distal portion thereof; and
  - a connector defining a third plane intersecting said first plane and said second plane, wherein said connector comprises a cutting member at a distal portion thereof, and wherein said first camming surface and said second camming surface are configured to engage said first jaw and said second jaw respectively to transition said end effector to said approximated configuration.

13. The surgical instrument of claim 12, wherein at least one of said first bendable portion and said second bendable portion is fabricated from an elastic alloy.

14. The surgical instrument of claim 12, wherein said elongate shaft comprises a bendable portion.

15. The surgical instrument of claim 12, wherein at least one of said first jaw and said second jaw comprises an electrode.

16. The surgical instrument of claim 12, wherein said first jaw comprises a first channel configured to receive said first camming surface.

17. The surgical instrument of claim 16, wherein said second jaw comprises a second channel configured to receive said second camming surface.

18. The surgical instrument of claim 12, wherein at least one of said first bendable portion and said second bendable portion comprises a plurality of cutout portions.

19. The surgical instrument of claim 18, wherein each said cutout portion comprises a first region and a second region, wherein said first region is narrower than said second region, and wherein said second region is further away from said connector than said first region.

20. An end effector for use with a surgical instrument, said end effector comprising:
a first jaw;
a second jaw, wherein said first jaw is movable relative to said second jaw to transition said end effector between an open configuration and an approximated configuration to clamp tissue between said first jaw and said second jaw; and
a camming assembly movable along a curved path, said camming assembly comprising:
- a first camming member, wherein said first camming member comprises:
  - a first distal camming portion;
  - a first proximal camming portion; and
  - a first flexible portion extending between said first distal camming portion and said first proximal camming portion;
- a second camming member; and
- a connector at least partially disposed between said first camming member and said second camming member, wherein said connector comprises a cutting member at a distal portion thereof, and wherein said camming assembly is movable relative to said end effector to exert a camming force against said first jaw and said second jaw to transition said end effector to said approximated configuration.

21. The surgical instrument of claim 20, wherein said first flexible portion comprises a plurality of recesses.

* * * * *

UNITED STATES PATENT AND TRADEMARK OFFICE
CERTIFICATE OF CORRECTION

| | | |
|---|---|---|
| PATENT NO. | : 9,456,864 B2 | |
| APPLICATION NO. | : 14/171035 | |
| DATED | : October 4, 2016 | |
| INVENTOR(S) | : Witt et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 214 days.

Signed and Sealed this

Twenty-fifth Day of September, 2018

Andrei Iancu
*Director of the United States Patent and Trademark Office*